United States Patent
Van Der Louw et al.

(10) Patent No.: US 7,812,036 B2
(45) Date of Patent: *Oct. 12, 2010

(54) ANDROGENS

(75) Inventors: Jaap Van Der Louw, Oss (NL); Neeltje Miranda Teerhuis, Oss (NL); Johannes Petrus Maria Lommerse, Oss (NL); Herman Thijs Stock, Oss (NL); Pedro Harold Han Hermkens, Oss (NL)

(73) Assignee: N.V. Organon, Oss (NL)

( * ) Notice: Subject to any disclaimer, the term of this patent is extended or adjusted under 35 U.S.C. 154(b) by 230 days.

This patent is subject to a terminal disclaimer.

(21) Appl. No.: 11/587,192

(22) PCT Filed: Apr. 21, 2005

(86) PCT No.: PCT/EP2005/051766
§ 371 (c)(1),
(2), (4) Date: Oct. 20, 2006

(87) PCT Pub. No.: WO2005/102998
PCT Pub. Date: Nov. 3, 2005

(65) Prior Publication Data
US 2007/0225352 A1 Sep. 27, 2007

Related U.S. Application Data

(60) Provisional application No. 60/565,043, filed on Apr. 23, 2004.

(30) Foreign Application Priority Data

Apr. 23, 2004 (EP) .................. 04101700

(51) Int. Cl.
*A61K 31/4439* (2006.01)
*C07D 401/06* (2006.01)
(52) U.S. Cl. .................. 514/339; 546/277.7
(58) Field of Classification Search .............. 546/277.7; 514/339
See application file for complete search history.

(56) References Cited

U.S. PATENT DOCUMENTS

| | | | |
|---|---|---|---|
| 4,059,583 A | 11/1977 | McComsey et al. | |
| 5,180,400 A | 1/1993 | Baudry et al. | |
| 5,482,960 A | 1/1996 | Berryman et al. | |
| 5,767,139 A | 6/1998 | Maw et al. | |
| 5,938,792 A | 8/1999 | Lang et al. | |
| 5,969,155 A | 10/1999 | Eturi et al. | |
| 2003/0195244 A1 | 10/2003 | Hsieh et al. | |
| 2004/0224973 A1 | 11/2004 | Dillon et al. | |

FOREIGN PATENT DOCUMENTS

| | | |
|---|---|---|
| DE | 2559211 | 7/1976 |
| EP | 409 025 | 7/1990 |
| EP | 303 306 | 3/1993 |
| EP | 460 996 | 9/1994 |
| EP | 876 815 | 1/2002 |
| EP | 1 466 902 1 A | 10/2004 |
| JP | 63313770 | 12/1998 |
| WO | WO 92/18093 | 10/1992 |
| WO | WO 98/23610 | 6/1998 |
| WO | WO 99/43651 | 9/1999 |
| WO | WO 99/43672 | 9/1999 |
| WO | WO 00/012475 | 3/2000 |
| WO | WO 03/011302 A | 2/2003 |
| WO | WO 03/064387 A | 8/2003 |
| WO | WO 2004/041782 A | 5/2004 |

OTHER PUBLICATIONS

International Search Report and Written Opinion for PCT/EP2005/051766 dated Aug. 5, 2005.
Chengalvala et al., "Selective Androgen Receptor Modulators," *Expert Opin. Ther. Patents* 13 (2003) 59-66.
Dobbs, et al., "Synthesis of Novel Indole Derivatives: Variations in the Bartoli Reaction," *Synlett* 10 (1999) 1594-1596.
Fisher et al., "Meta-Substituent Effects on Benzyl Free-Radical Stability," *J. Org. Chem.* 55 (1990) 1040-1043.
Schoonen et al., "Hormonal Properties of Norethisterone. 7α-methyl-norethisterone and their Derivatives," *J. Steroid Biochem. Molec. Biol.* 74 (2002) 213-222.
Terent'ev et al., *Zhurnal Obshchei Khimii* 29 (1959) 2541-51 (English language abstract attached thereto).

*Primary Examiner*—Patricia L Morris
(74) *Attorney, Agent, or Firm*—Susan L. Hess

(57) ABSTRACT

The compounds of the subject invention have a structure according to formula I:

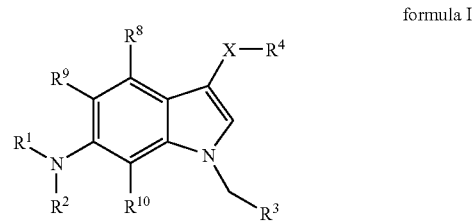

formula I wherein each of the substituents is given the definition as set forth in the specification and claims, or a salt or hydrate form thereof.

13 Claims, No Drawings

ANDROGENS

CROSS REFERENCE TO RELATED APPLICATIONS

This application is a 371 of PCT/EP05/51766, filed Apr. 21, 2005, which claims the benefit of U.S. Provisional Application No. 60/565,043, filed Apr. 23, 2004.

FIELD OF THE INVENTION

The present invention relates to the field of male and female hormone replacement therapy (HRT), male contraception, and therapy of androgen-receptor related conditions, disorders and diseases, and other androgen-related treatments.

The subject invention provides novel non-steroidal androgens, processes for their preparation, and their use in therapy.

BACKGROUND OF THE INVENTION

Compounds possessing androgenic activity are useful in androgen-related treatments and the treatment of androgen-receptor related conditions, disorders and diseases such as male hypogonadism including late-onset hypogonadism associated with ageing. Compounds possessing androgenic activity can also be used in combination with (or without) progestagens for male contraception.

Currently, steroidal androgens are the only agents available for the treatment of androgen-receptor related conditions. However, significant limitations with regard to efficacy, pharmacokinetic profile and safety have compromised the therapeutic success of these compounds.

Examples of non-steroidal androgens are described in e.g. Expert Opinion (2003), 13(1):59-66 (Chengalvala, M. et al). Other non-steroidal androgens are described in PCT International patent application number WO/EP03/50783.

The subject invention relates to new indole derivatives, their preparation and their use for the treatment of androgen-receptor related conditions, disorders or diseases and other androgen related treatments.

WO 99/43672 and WO 99/43651 describe indole compounds which are inhibitors of phospholipase A2 and which have a different substitution pattern than the compounds of the subject invention.

US 2003/195244 describes indole compounds with anti-cancer activity which also have a different substitution pattern than the compounds of the subject invention.

DETAILED DESCRIPTION OF THE INVENTION

The subject invention relates to indole derivatives, their preparation and their use for the treatment of androgen-receptor related conditions, disorders or diseases and other androgen related treatments.

The subject invention provides non-steroidal compounds with high affinity for the androgen receptor.

The compounds of the subject invention have a structure according to formula I:

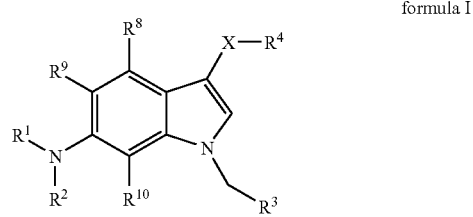

formula I wherein
X is S or $SO_2$;
$R^1$ is (1C-6C)alkyl, (3C-6C)alkenyl, or (3C-6C)alkynyl, each optionally substituted with (3C-6C)cycloalkyl, OH, OC(O)(1C-4C)alkyl, (1C-4C)alkoxy, halogen, cyano, formyl, C(O)(1C-4C)alkyl, $CO_2H$, $CO_2$(1C-4C)alkyl, C(O)$NR^5R^6$, S(O)(1C-4C)alkyl or $S(O)_2$(1C-4C)alkyl;
$R^2$ is hydrogen, (1C-4C)alkyl or C(O)(1C-4C)alkyl;
$R^3$ is a phenyl group optionally substituted with (1C-4C)alkyl, (1C-4C)fluoroalkyl, (1C-4C)alkoxy, (1C-4C)fluoroalkoxy, halogen, cyano or nitro;
or $R^3$ is a 5- or 6-membered aromatic heterocyclic ring structure optionally substituted with (1C-4C)alkyl, (1C-4C)fluoroalkyl, (1C-4C)alkoxy, halogen or cyano;
$R^4$ is a phenyl group or an aromatic 6-membered heterocycle, substituted at the ortho position with 1-hydroxy(1C-4C)alkyl, (1C-4C)alkoxy, C(O)(1C-4C)alkyl, $CO_2$(1C-4C)alkyl, C(O)$NH_2$, cyano, nitro, or CH=$NOR^7$, and optionally further substituted with (1C-2C)alkyl, (1C-2C)fluoroalkyl or halogen;
or $R^4$ is 2-pyridyl optionally substituted with (1C-2C)alkyl, (1C-2C)fluoroalkyl or halogen;
$R^5$ and $R^6$ are independently hydrogen or (1C-4C)alkyl;
$R^7$ is hydrogen or C(O)(1C-4C)alkyl;
$R^1$, $R^9$, $R^{10}$ are independently hydrogen, (1C-2C)alkyl, fluoro or chloro;

or a salt or hydrate form thereof

A more specific embodiment of the invention is according to the definition above, but whereby $R^8$, $R^9$, $R^{10}$ are hydrogen In one embodiment, a compound of the subject invention is characterised in that:
$R^2$ is hydrogen, (1C-2C)alkyl or C(O)$CH_3$;
$R^3$ is a phenyl group optionally substituted at the 3-, 4- or 5-position with (1C-2C)alkyl, (1C-2C)fluoroalkyl, (1C-2C)alkoxy, (1C-2C)fluoroalkoxy, halogen, cyano or nitro;
or $R^3$ is a 5- or 6-membered aromatic heterocyclic ring structure optionally substituted with (1C-2C)alkyl, (1C-2C)fluoroalkyl, (1C-2C)alkoxy, halogen or cyano;
$R^4$ is a phenyl group or an aromatic 6-membered heterocycle, substituted at the ortho position with hydroxymethyl, methoxy, C(O)$CH_3$, $CO_2CH_3$, C(O)$NH_2$, cyano, nitro or CH=$NOR^7$, and optionally fnther substituted with (1C-2C)alkyl, (1C-2C)fluoroalkyl or halogen;
or $R^4$ is 2-pyridyl optionally substituted with (1C-2C)alkyl, (1C-2C)fluoroalkyl or halogen; and
$R^7$ is hydrogen or C(O)(1C-2C)alkyl;
$R^8$, $R^9$, $R^{10}$ are hydrogen.

In another embodiment, a compound of the invention is characterised in that:
X is S;
$R^1$ is (1C-4C)alkyl, (3C-6C)alkenyl, or (3C-6C)alkynyl, each optionally substituted with (3C-6C)cycloalkyl, OH, OC(O)(1C-2C)alkyl, (1C-2C)alkoxy, halogen, cyano, formyl, C(O)(1C-2C)alkyl, $CO_2H$ or $CO_2$(1C-2C)alkyl;
$R^3$ is a phenyl group optionally substituted at the 3-, 4- or 5-position with methyl, $CF_3$, methoxy, $OCF_3$, fluoro, chloro, cyano or nitro;
or $R^3$ is a 5- or 6-membered aromatic heterocyclic ring structure optionally substituted with methyl, $CF_3$, methoxy, fluoro, chloro or cyano;
$R^4$ is a phenyl group or an aromatic 6-membered heterocycle, substituted at the ortho position with hydroxymethyl, methoxy, C(O)$CH_3$, $CO_2CH_3$, C(O)$NH_2$, cyano, nitro or CH=NOH;
or $R^4$ is 2-pyridyl optionally substituted with methyl, $CF_3$, fluoro or chloro;

$R^8$, $R^9$, $R^{10}$ are hydrogen.

In yet another embodiment, a compound of the invention is characterised in that $R^8$, $R^9$, $R^{10}$ and $R^2$ are hydrogen.

It a specific embodiment a compound of the invention is characterised in that $R^3$ is a phenyl group optionally substituted at the 3-, 4- or 5-position with methyl, $CF_3$, methoxy, $OCF_3$, fluoro, chloro, cyano or nitro and $R^8$, $R^9$, $R^{10}$ are hydrogen.

In another embodiment, a compound of the invention is characterised in that $R^4$ is a phenyl group substituted at the ortho position with hydroxymethyl, methoxy, $C(O)CH_3$, $CO_2CH_3$, $C(O)NH_2$, cyano, nitro or CH=NOH and $R^8$, $R^9$, $R^{10}$ are hydrogen.

In yet another embodiment of the invention is characterised in that:
$R^1$ is (1C-4C)alkyl optionally substituted with OH, (1C-2C) alkoxy, cyano, C(O)(1C-2C)alkyl or $CO_2$(1C-2C)alkyl;
$R^3$ is a phenyl group, optionally substituted at the 3-, 4- or 5-position with fluoro or chloro;
$R^4$ is a phenyl group, substituted at the ortho position with hydroxymethyl, cyano or nitro;
and,
$R^8$, $R^9$, $R^{10}$ are hydrogen.

It is also an embodiment of the invention that a compound of the invention is characterised in that:
$R^1$ is (1C-4C)alkyl optionally substituted with OH, methoxy, cyano, $C(O)CH_3$ or $CO_2CH_3$ and $R^4$ is a 2-nitrophenyl group and
$R^8$, $R^9$, $R^{10}$ are hydrogen In a specific embodiment, a compound of the invention is selected from the group consisting of:
[1-(3,5-difluoro-benzyl)-3-(2-nitro-phenylsulfanyl)-1H-indol-6-yl]-methyl-amine;
[1-(3,5-difluoro-benzyl)-3-(2-nitro-phenylsulfanyl)-1H-indol-6-ylamino]-acetonitrile;
1-[1-(3,5-difluoro-benzyl)-3-(2-nitro-phenylsulfanyl)-1H-indol-6-ylamino]-propan-2-one;
2-[1-(3,5-difluoro-benzyl)-3-(2-nitro-phenylsulfanyl)-1H-indol-6-ylamino]-ethanol; and
[1-(3,5-difluoro-benzyl)-3-(2-nitro-phenylsulfanyl)-1H-indol-6-yl]-(2-methoxy-ethyl)-amine.

In yet another embodiment of the invention is characterised in that:
$R^1$ is (1C-4C)alkyl optionally substituted with OH, methoxy, cyano, $C(O)CH_3$ or $CO_2CH_3$ and $R^4$ is a 2-cyanophenyl group and $R^8$, $R^9$, $R^{10}$ are hydrogen.

In a specific embodiment, the compound of the invention is 2-[1-(3,5-difluoro-benzyl)-6-methylamino-1H-indol-3-ylsulfanyl]-benzonitrile.

In a further embodiment, a compound of the invention is characterised in that $R^3$ is a 5- or 6-membered aromatic heterocyclic ring structure optionally substituted with methyl $CF_3$, methoxy, fluoro, chloro or cyano and $R^8$, $R^9$, $R^{10}$ are hydrogen.

In an additional embodiment, a compound of the invention is characterised in that $R^4$ is a phenyl group substituted at the ortho position with hydroxymethyl, methoxy, $C(O)CH_3$, $CO_2CH_3$, $C(O)NH_2$, cyano, nitro or CH=NOH and $R^8$, $R^9$, $R^{10}$ are hydrogen.

In one embodiment, a compound of the invention is characterised in that:
$R^1$ is (1C-4C)alkyl optionally substituted with OH, (1C-2C) alkoxy, cyano, C(O)(1C-2C)alkyl or $CO_2$(1C-2C)alkyl;
$R^3$ is a 5- or 6-membered aromatic heterocyclic ring structure optionally substituted with methyl, fluoro, chloro or cyano;
and $R^4$ is a phenyl group, substituted at the ortho position with hydroxymethyl, cyano or nitro and,
$R^8$, $R^9$, $R^{10}$ are hydrogen.

In another embodiment, a compound of the invention is characterised in that $R^3$ is selected from the group consisting of pyridin-2-yl, pyridin-3-yl, pyridin-4-yl, pyrimidin-2-yl, pyrimidin-5-yl, furan-2-yl, furan-3-yl, oxazol-4-yl, isoxazol-3-yl, and thiazol-4-yl, each optionally substituted with methyl, fluoro, chloro or cyano and $R^8$, $R^9$, $R^{10}$ are hydrogen.

In yet another embodiment, a compound of the invention is characterised in that:
$R^1$ is (1C-4C)alkyl optionally substituted with methoxy, cyano, $C(O)CH_3$ or $CO_2CH_3$;
$R^3$ is selected from the group consisting of pyridin-2-yl, pyridin-3-yl, pyridin-4-yl and pyrimidin-5-yl; and
$R^4$ is a 2-nitrophenyl group and,
$R^8$, $R^9$, $R^{10}$ are hydrogen.

In a specific embodiment, a compound of the invention is methyl-[3-(2-nitro-phenylsulfanyl)-1-pyridin-2-ylmethyl-1H-indol-6-yl]-amine or methyl-[3-(2-nitro-phenylsulfanyl)-1-pyridin-3-ylmethyl-1H-indol-6-yl]-amine.

In a further embodiment, a compound of the invention is characterised in that:
$R^1$ is (1C-4C)alkyl optionally substituted with methoxy, cyano, $C(O)CH_3$ or $CO_2CH_3$;
$R^3$ is selected from the group consisting of furan-2-yl, furan-3-yl, oxazol-4-yl, isoxazol-3-yl, and thiazol-4-yl, each optionally substituted with methyl, fluoro or chloro; and
$R^4$ is a 2-nitrophenyl group and,
$R^8$, $R^9$, $R^{10}$ are hydrogen.

In yet a further embodiment, a compound of the invention is characterised in that $R^3$ is furan-2-yl or furan-3-yl and $R^8$, $R^9$, $R^{10}$ are hydrogen.

In a specific embodiment, a compound of the invention is [1-furan-2-ylmethyl-3-(2-nitro-phenylsulfanyl)-1H-indol-6-yl]-methyl-amine or [1-furan-3-ylmethyl-3-(2-nitro-phenylsulfanyl)-1H-indol-6-yl]-methyl-amine.

The terms used in the description of the subject invention have the following meaning:

Alkyl is a branched or unbranched alkyl group, for example methyl, ethyl, propyl, isopropyl, butyl, sec-butyl, tert-butyl, hexyl, and the like.

Alkenyl is a branched or unbranched alkenyl group, for example ethenyl, allyl, methallyl, butenyl, and the like.

Alkynyl is a branched or unbranched alkynyl group, for example ethynyl, 2-propynyl, 2-butynyl, 3-butynyl, and the like.

Fluoroalkyl is an alkyl group substituted with one or more fluorine atoms.

Cycloalkyl is a cyclized unbranched alkyl group, such as cyclopropyl, cyclobutyl, cyclopentyl and the like.

Alkoxy is a branched or unbranched alkyloxy group, for example methyloxy (methoxy), ethyloxy (ethoxy), propyloxy, isopropyloxy, butyloxy, sec-butyloxy, tert-butyloxy and the like.

Fluoroalkoxy is an alkoxy group substituted with one or more fluorine atoms.

Halogen refers to fluorine, chlorine, bromine or iodine.

The prefixes (1C-6C), (3C-6C) etc. have the usual meaning to restrict the meaning of the indicated group to those with 1 to 6, 3 to 6 etc. carbon atoms.

As used herein, the term "substituted" means that one or more hydrogen atom(s) may be replaced by one or more of the indicated substituent(s) if such replacement(s) results in a stable compound.

When $R^3$ is a 5- or 6-membered aromatic heterocyclic ring structure, it is attached through a carbon atom of the heterocycle.

Likewise, when $R^4$ is an aromatic 6-membered heterocycle, it is attached through a carbon atom to the X linker which is attached to C-3 of the indole.

A compound according to the invention is a compound as defined above, a salt thereof, a hydrate thereof or a prodrug thereof.

In those cases that a compound of the invention contains a nitrogen atom of suitable basicity, the compound may be used as a free base or as a pharmaceutically acceptable salt.

The term pharmaceutically acceptable salt represents those salts which are, within the scope of medical judgement, suitable for use in contact with the tissues of humans and/or animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like.

Prodrugs represent compounds which are rapidly transformed in vivo to the parent compound of the above formula.

The androgen receptor affinity and efficacy of the compounds according to the invention make them suitable for use in androgen-related treatments and the treatment of androgen-receptor related conditions, disorders and diseases.

Compounds of the subject invention possessing androgenic activity can also be used in combination with (or without) progestagens for male contraception.

Typical androgen receptor-related treatments are treatment for androgen insufficiency, or male or female hormone replacement therapy, e.g. for male hypogonadism including late-onset hypogonadism associated with ageing.

Thus the invention pertains to a method of treatment of androgen insufficiency, by administering to a male or female human or animal an effective amount of any of the compounds of the subject invention.

In the context of the invention, the term "androgen insufficiency" is to be understood to pertain to all kinds of diseases, disorders, conditions and symptoms in which a male or female suffers from low testosterone levels. Specifically, the androgen insufficiency to be treated by a compound of the invention is the reduction of the testosterone level which may occur in an ageing male (the compound of the invention is then used for male hormone replacement therapy), or when a male is subject to male contraception.

In the context of male contraception, the compound of the invention especially serves to normalise the hypoandrogenic effect of regimens of male hormone contraception in which a sterilitant such as a progestagen or LHPH (Quteinizing hormone releasing hormone) is used, or it is used as the sole male contraceptive substance.

The compounds of the invention may further be useful in the treatment or prevention of osteoporosis, bone fracture repair, sarcopenia, frailty, skin aging, male hypogonadism, female sexual dysfunction, female postmenopausal symptoms, cardiovascular disease, aplastic anemia, muscular atrophy, lipodystrophy, reduced muscle strength and function, side effects of chemotherapy, chronic fatigue syndrome, benign prostate hyperplasia (BPPH), cachexia, chronic catabolic state, cognitive impairment, and others.

Thus, the subject invention provides any one of the compounds of the subject invention for use in therapy.

The subject invention further provides a pharmaceutical composition comprising a compound according the invention and a pharmaceutically acceptable carrier. In one embodiment, the pharmaceutical composition is for the treatment of a disease, disorder or condition treatable with androgens. In another embodiment, the pharmaceutical composition is for the treatment of an androgen-receptor related disease, disorder or condition. In yet another embodiment, the pharmaceutical composition is for male contraception.

The subject invention further involves a use of a compound of the invention for the manufacture of a medicament. In one embodiment, the use is for the manufacture of a male contraceptive. In another embodiment, the use is for the manufacture of a medicament for the treatment of a condition, disorder or disease treatable with androgens.

In yet another embodiment, the use is for the manufacture of a medicament for the treatment of an androgen-receptor related condition, disorder or disease.

The subject invention further envisages a method of treating a condition, disorder or disease treatable with androgens comprising administering a pharmaceutically effective amount of a compound according to the invention to a subject in need thereof.

The subject invention also provides a method of treating an androgen-receptor related condition, disorder or disease comprising administering a pharmaceutically effective amount of a compound according to the invention to a subject in need thereof.

The subject invention further encompasses a method of male contraception comprising administering a pharmaceutically effective amount of a compound according to the invention to a subject in need thereof.

The compounds of the invention may be administered in conjunction with estrogens, androgens, progestagens, and other suitable compounds such as folic acid, vitamins, minerals etc.

Methods to determine receptor activation as well as in vitro assays to determine biological activity of the compounds are well known. In general, expressed receptor (or a functional part thereof) is treated with a compound of the invention and stimulation of a functional response is measured.

To measure a functional response, isolated DNA encoding the androgen receptor gene, preferably the human receptor, is expressed in suitable host cells. Such a cell might be the Chinese Hamster Ovary (CHO) cell, but other cells are also suitable. Preferably the cells are of mammalian origin. Methods to construct recombinant androgen receptor-expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein.

Techniques for site-directed mutagenesis, ligation of additional sequences, PCR, and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided through the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with a compound of the invention to observe stimulation of a functional response.

Alternatively, isolated cytosol containing the expressed receptor may be used to measure binding of a compound of the invention.

For measurement of binding, radioactive or fluorescence-labelled compounds may be used. As reference compound, the native hormone, or other compounds binding to the receptor, can be used. As an alternative, competition binding assays can be performed as well.

Another assay involves screening for compounds of the invention by determining regulation of receptor-mediated natural target gene mRNA, i.e. genes regulated by the receptor through binding of the receptor in the promoter region of the gene. The levels of target gene mRNA will be reduced or increased, depending on the inhibitory or stimulating effect of a compound of the invention upon binding to the receptor.

In addition to direct measurement of mRNA levels in the exposed cells, cells can be used which in addition to transfection with receptor encoding DNA have also been transfected with a second DNA encoding a reporter gene, the expression of which responds to binding of the receptor towards responsive elements in the promoter of the particular reporter gene. Such responsive elements might be classical hormone-responsive elements, well known in the art and described e.g. in Beato, M, Chalepakis, G, Schauer, M, Slater, EP J. Steroid Biochem. 5 (1989)737-47 or might be constructed in such a way that they are connected to novel responsive elements. In general, reporter gene expression might be controlled by any response element reacting to androgen receptor binding. Suitable reporter genes are e.g. LacZ, alkaline phosphatase, firefly luciferase and green fluorescence protein.

Basically any transactivation assay in mammalian cells (cell line or primary culture) that can yield information about the possible receptor activation can be used for the purpose of selecting potent and suitable ligands. The added value of using several cell systems, with cells which originate from different organs, will be that information on the potential tissue specificity of the ligands is obtained. Without limitation, examples of cells frequently used to this end are, besides CHO cells, e.g. CV1 cells, MCF7 cells, T47D cells, mouse muscle cell line C2C12, and human prostate cell lines LNCaP, PC3, MDA PCa2a and PCa2b, HeLa cells, and pituitary cells.

The skilled artisan will further recognize that the selection of compounds of the subject invention depends on the potencies of these compounds. For example, a compound with a potency of about 0.1%, when dihydrotestosterone represents 100%, is, generally, considered a candidate for drug selection. In one embodiment, this value is above about 1%. In a more specific embodiment, compounds will have potencies of about 10% or above.

Suitable routes of administration for the compounds of the subject invention (also called active ingredient) are oral, rectal, nasal, topical (including transdermal, buccal and sublingual), vaginal or parenteral (including subcutaneous, intramuscular, intravenous and intradermal) administration or administration via an implant. In a specific embodiment, the compounds can be administered orally.

The exact dose and regimen of administration of the active ingredient, or a pharmaceutical composition thereof, will necessarily be dependent upon the therapeutic effect to be achieved (e.g. contraception, HRT) and may vary with the particular compound, the route of administration, and the age and condition of the individual subject to whom the medicament is to be administered.

A dosage for humans is likely to contain 0.0001-25 mg per kg body weight. The desired dose may be presented as one dose or as multiple sub-doses administered at appropriate intervals throughout a day or days.

The present invention thus also relates to pharmaceutical compositions comprising a compound according to Formula I in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy, for example, using methods such as those described in Gennaro et al., Remington's Pharmaceutical Sciences (18th ed., Mack Publishing company, 1990, see especially Part 8: *Pharmaceutical Preparations and Their Manufacture*).

Such methods include the step of bringing in association the active ingredient with any auxiliary agent. The auxiliary agent(s), also named accessory ingredient(s), include those conventional in the art (Gennaro, supra), such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragees or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for the use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The compounds of the invention can also be administered in the form of devices consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in EP 303,306.

The compounds of the invention can also be administered in the form of a vaginal ring such as described for example in EP 876815.

The compounds of the invention can be produced by various methods known in the art of organic chemistry in general.

More specifically the routes of synthesis as illustrated in the following schemes and examples can be used. In the schemes and examples the following abbreviations are used:

| Boc | tert-butoxycarbonyl |
| g | gram |
| h | hour |
| M | molar |
| NMR | nuclear magnetic resonance |

The compounds of the invention can be prepared from readily available starting materials using standard methods known in the art. A convenient starting material is for example 6-nitroindole. This compound can easily be prepared by known methods (e.g. Terent'ev, A. P. et al, Zhurnal Obshchei Khimii (1959), 29 2541-51; CAN 54:56386) or be obtained commercially. 6-Nitroindole can be processed to compounds of the invention in various ways, methods of preparation mostly being dictated by the precise nature of the substituents.

In the description of the compounds of the invention, the following numbering is used:

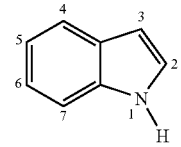

Representative methods of preparation of the compounds of the invention are described in Schemes 1-6.

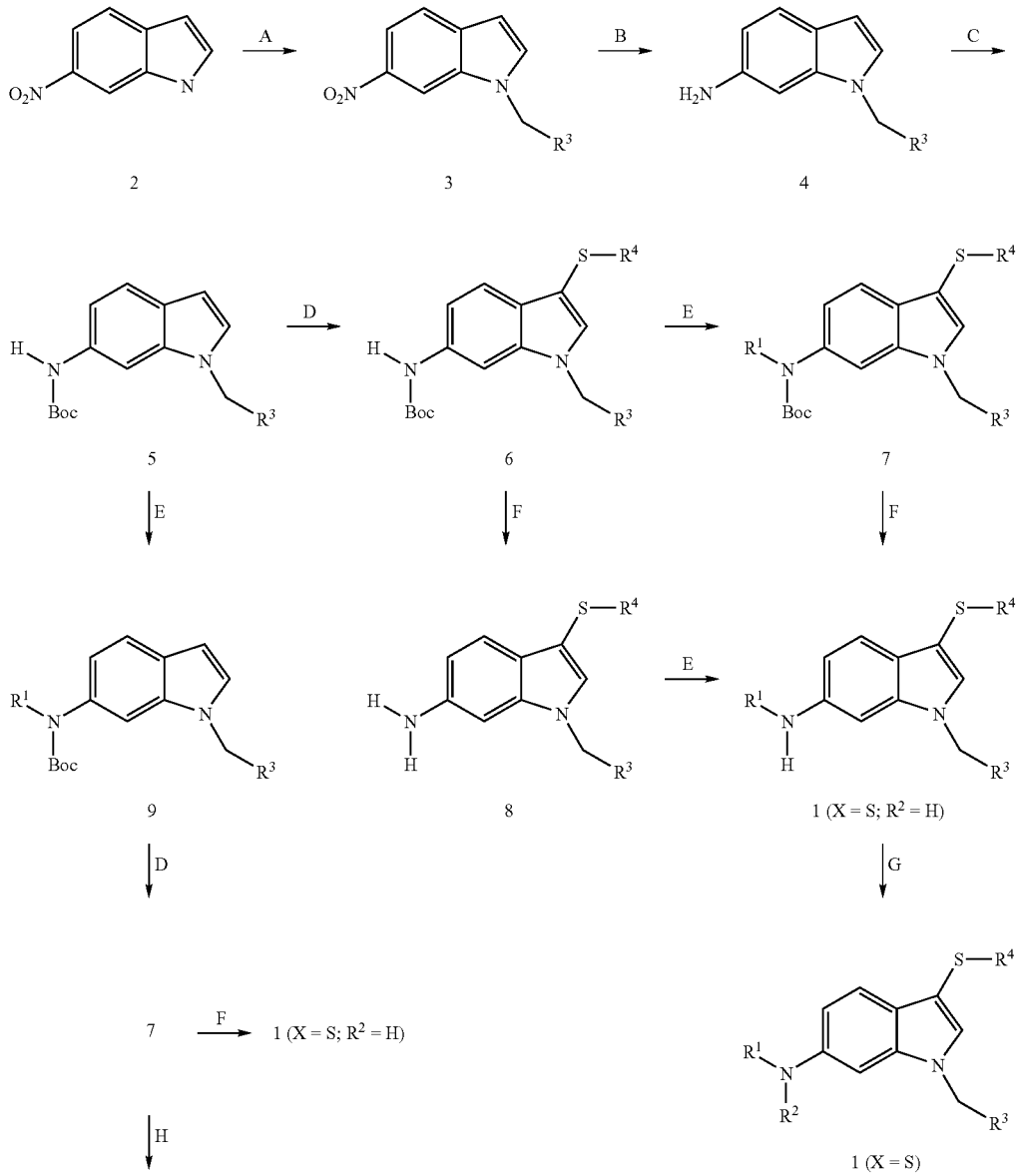

Scheme 1. Example of general synthesis of compounds of the invention.

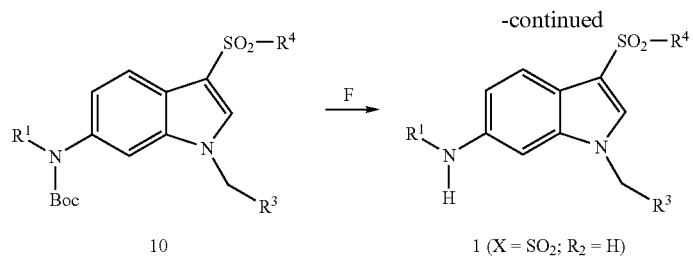
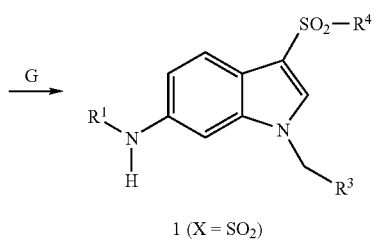

Conditions (reagents mentioned are examples only): A: $R^3CH_2Y$ (Y=Cl, Br, p-toluenesulfonyloxy, or methanesulfonyloxy)/base. B: Palladium on carbon/hydrogen gas, or tin (II)chloride/hydrochloric acid, or iron powder/ammonium chloride. C: Di-tert-butyl dicarbonate/base. D: $ClSR^4$, or $HSR^4$/chlorine, or $HSR^4$/sulfuryl chloride. E: $R^1Y$ (Y=Cl, Br, p-toluenesulfonyloxy, or methanesulfonyloxy)/base. F: Trifluoroacetic acid. G: $R^2Y$ (Y=Cl, Br, p-toluenesulfonyloxy, or methanesulfonyloxy)/base. H: m-Chloroperbenzoic acid.

Scheme 1 gives an example of a general synthesis route by which compounds of the invention can be prepared from 6-nitroindole 2. The procedure can be used for compounds in which $R^4$ is a phenyl group or an aromatic 6-membered heterocycle, substituted at the ortho position with e.g. (1C-4C)alkoxy, $CO_2$(1C-4C)alkyl, cyano or nitro, and optionally further substituted with (1C-2C)alkyl, (1C-2C)fluoroalkyl or halogen, or in which $R^4$ is 2-pyridyl optionally substituted with (1C-2C)alkyl, (1C-2C)fluoroalkyl or halogen.

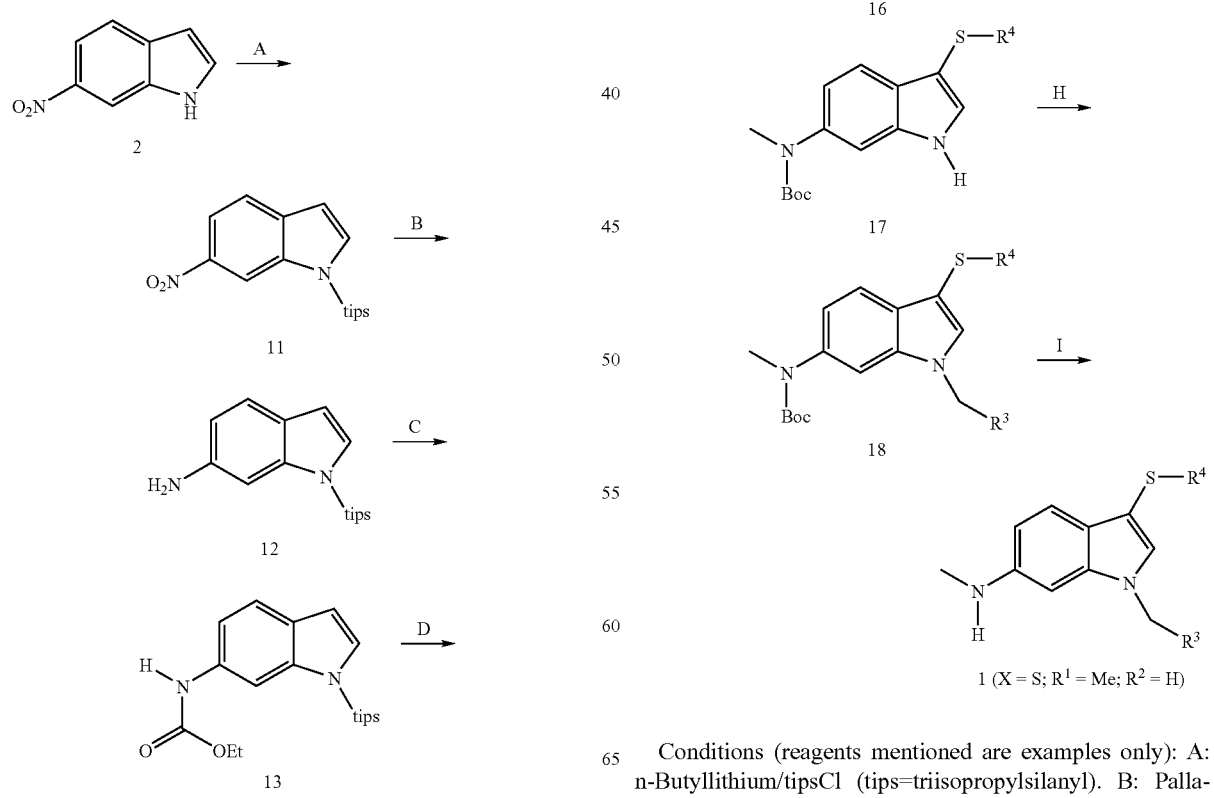

Conditions (reagents mentioned are examples only): A: n-Butyllithium/tipsCl (tips=triisopropylsilanyl). B: Palladium on carbon/hydrogen gas, or tin(II) chloride/hydrochloric acid, or iron powder/ammonium chloride. C: Ethyl chloroformate/diisopropylethylamine. D: Lithium aluminium hydride. E: Di-tert-butyl dicarbonate/base. F: ClSR$^4$, or HSR$^4$/chlorine, or HSR$^4$/sulfinyl chloride. G: Tetrabutylammonium fluoride. H: R$^3$CH$_2$Y (Y=Cl, Br, p-toluenesulfonyloxy, or methanesulfonyloxy)/base. I: Trifluoroacetic acid.

Reaction steps described can be carried out using standard methods known in the art. In the first step, the R$^3$—CH$_2$ group is introduced. Reduction of the nitro group at the 6-position and protection of the resulting amines 4 gives intermediates 5, which may serve as starting materials for the introduction of the R$^4$sulfanyl group at the 3-position. N-alkylation of the 6-NHBoc group in 6 gives 7 which can then be deprotected to afford compounds of the invention according to formula I (X=S; R$^2$=H). Optionally, deprotection can be carried out before N-alkylation via compounds 8.

Alternatively, N-alkylation of the 6-NHBoc group in 5 with R$^1$Y can be carried out before introduction of the R$^4$sulfanyl group at the 3-position. In that case compounds 7 can be obtained via compounds 9.

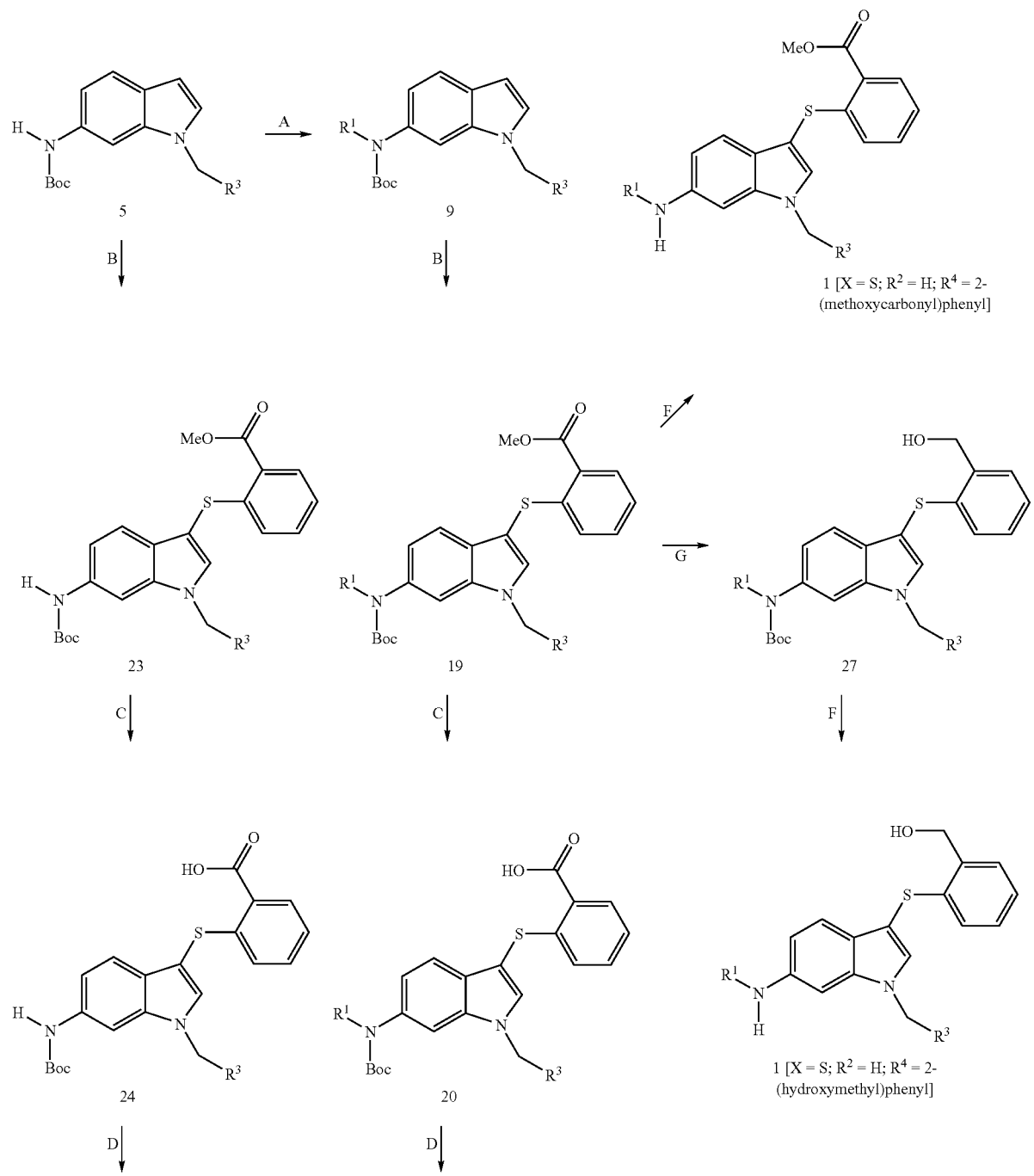

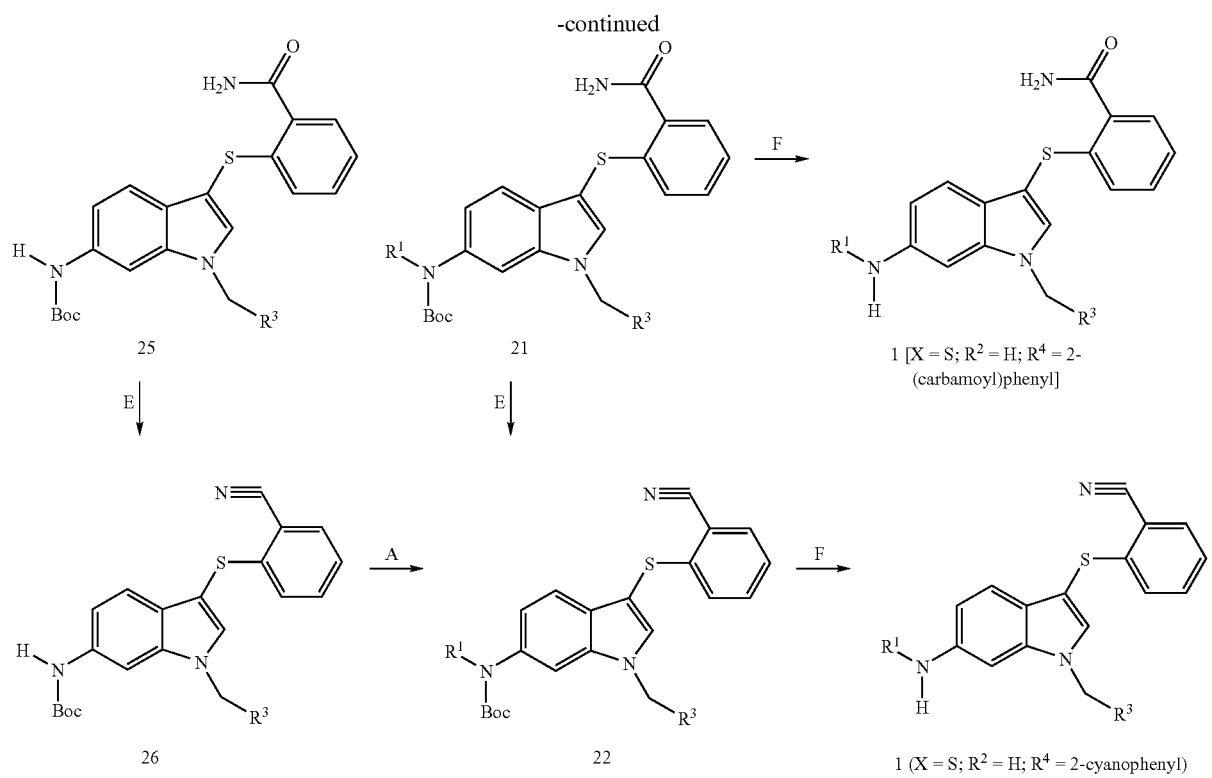

Conditions (reagents mentioned are examples only): A: R¹Y (Y=Cl, Br, p-toluenesulfonyloxy, or methanesulfonyloxy)/base. B: 2-Mercapto-benzoic acid methyl ester/chlorine. C: Lithium hydroxide/water. D: 2-(1H-benzotriazol-1-yl)-1,1,3,3-tetramethyluronium tetrafluoroborate/ammonium chloride/diisopropylethylamine. E: Trifluoromethanesulfonic anhydride. F: Trifluoroacetic acid. G: Lithium aluminium hydride.

6-NR¹Boc compounds 7 can be used as starting material for compounds of the invention in which X is $SO_2$. Oxidation gives sulfones 10 which can be deprotected to compounds of the invention 1 (X=$SO_2$; R²=H).

Optionally, compounds of the invention 1 (R²=H) may be processed further by N-alkylation or acylation to produce compounds of the invention with R²=(1C-4C)alkyl or C(O)(1C-4C)alkyl.

Alkylating agents required are commercially available or can be obtained by common methods. In some cases, they contain functional groups which need temporary protection. Likewise, reagents required for the introduction of the R⁴sulfanyl groups, e.g. the ClSR⁴ compounds mentioned in the legend of Scheme 1, are commercially available or can be obtained by common methods from readily available starting materials.

Scheme 2 gives an example of a possible synthesis route which allows preparation of compounds of formula I (R¹=methyl; R²=H) with various groups R³. Key steps involve the reduction of carbamate 13 to N-methyl compound 14 and the N-alkylation of synthetic intermediate 17 which can be used for the introduction of all types of substituents R³—CH₂.

Scheme 3, Scheme 4 and Scheme 5 give examples of synthesis routes which allow preparation of compounds of the invention 1 with R⁴ is a phenyl group or an aromatic 6-membered heterocycle, substituted at the ortho position with 1-hydroxy(1C-4C)alkyl, C(O)(1C-4C)alkyl, $CO_2$(1C-4C)alkyl, C(O)NH₂, cyano or CH=NOR⁷, and optionally further substituted with (1C-2C)alkyl, (1C-2C)fluoroalkyl or halogen.

For instance, 6-NR¹Boc compounds 9 can be converted to methyl esters 19 which may serve as starting materials for compounds of the invention 1 in which R⁴ is a 2-(methoxycarbonyl) phenyl group, a 2-(hydroxymethyl)phenyl group, a 2-(carbamoyl)phenyl group or a 2-cyanophenyl group (Scheme 3). These types of compounds can also be obtained from intermediates 23, 24, 25 and 26, respectively, by N-alkylation of the 6-NHBoc group followed by removal of the protecting group.

The hydroxymethyl group in compounds 27 may be oxidised to produce compounds 28 with R⁴ is 2-formylphenyl (Scheme 4). The latter can be reacted with an organometallic agent [e.g. (1C-3C)alkylmagnesium bromide] to compounds 29 wherein R⁴ is a phenyl group substituted at the ortho position with 1-hydroxy(1C-4C)alkyl, which in turn can be oxidised to compounds 30 with R⁴ is phenyl substituted at the ortho position with C(O)(1C-3C)alkyl. Deprotection of the 6-amino function in 29 and 30 affords compounds of the invention. Reaction of 28 with e.g. (4C)alkylmagnesium bromide followed by oxidation and deprotection provides compounds of the invention with R⁴ is phenyl substituted at the ortho position with C(O)(4C)alkyl.

The formyl group in compounds 28 may also be converted to a hydroxyiminomethyl group wherein the hydroxy group may further be acetylated (Scheme 5). Deprotection of the 6-NR¹Boc group in 31 and 32, respectively, provides compounds of the invention wherein R⁴ is a phenyl group, substituted at the ortho position with CH=NOR⁷[R⁷=H or C(O)(1C-4C)alkyl].

Scheme 4. Variation of R⁴ (part 2).
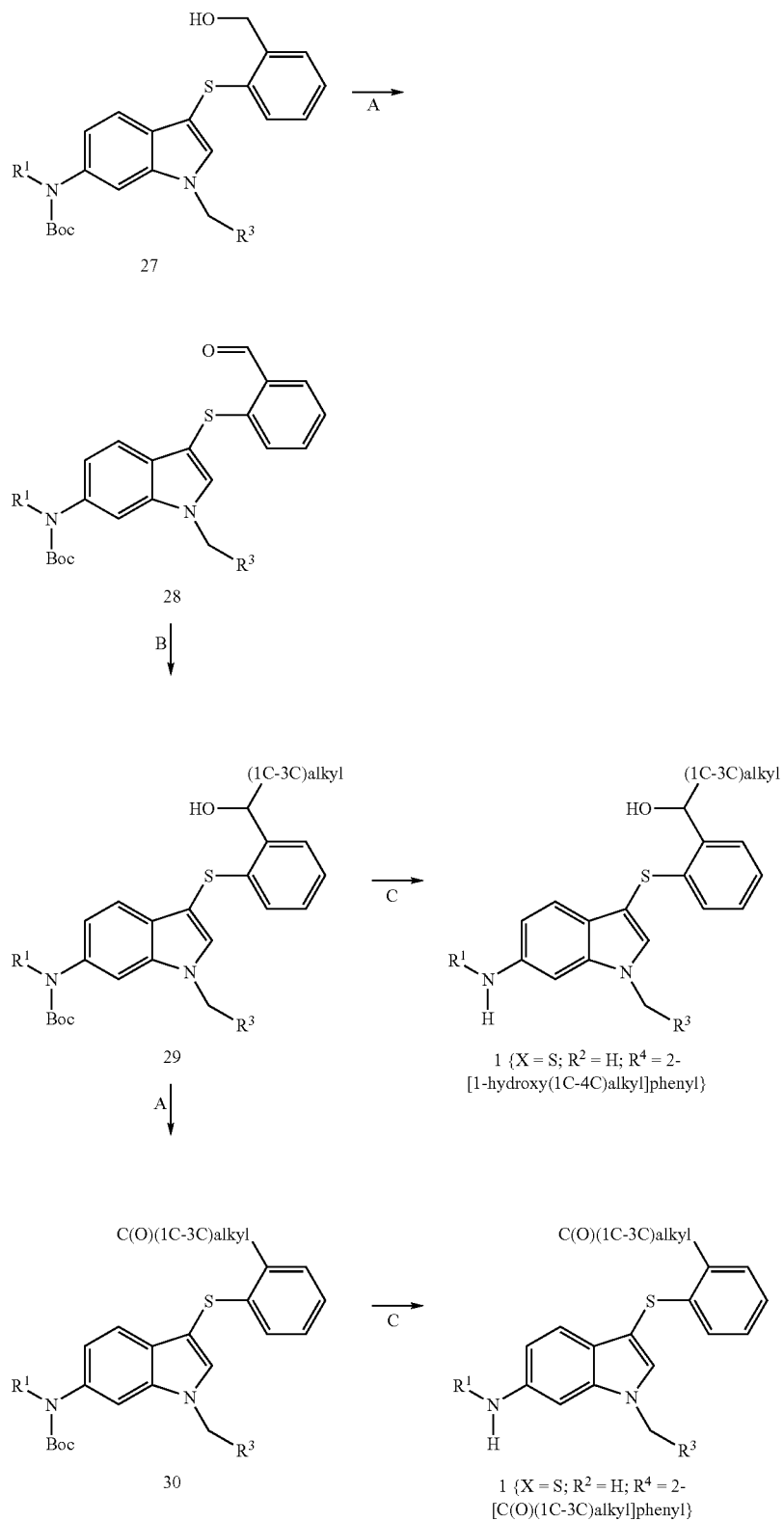
Conditions (reagents mentioned are examples only): A: Tetrapropylammonium perruthenate/4-methylmorpholine N-oxide. B: (1C-3C)Alkyl magnesium bromide. C: Trifluoroacetic acid.

Scheme 5. Variation of R⁴ (part 3).

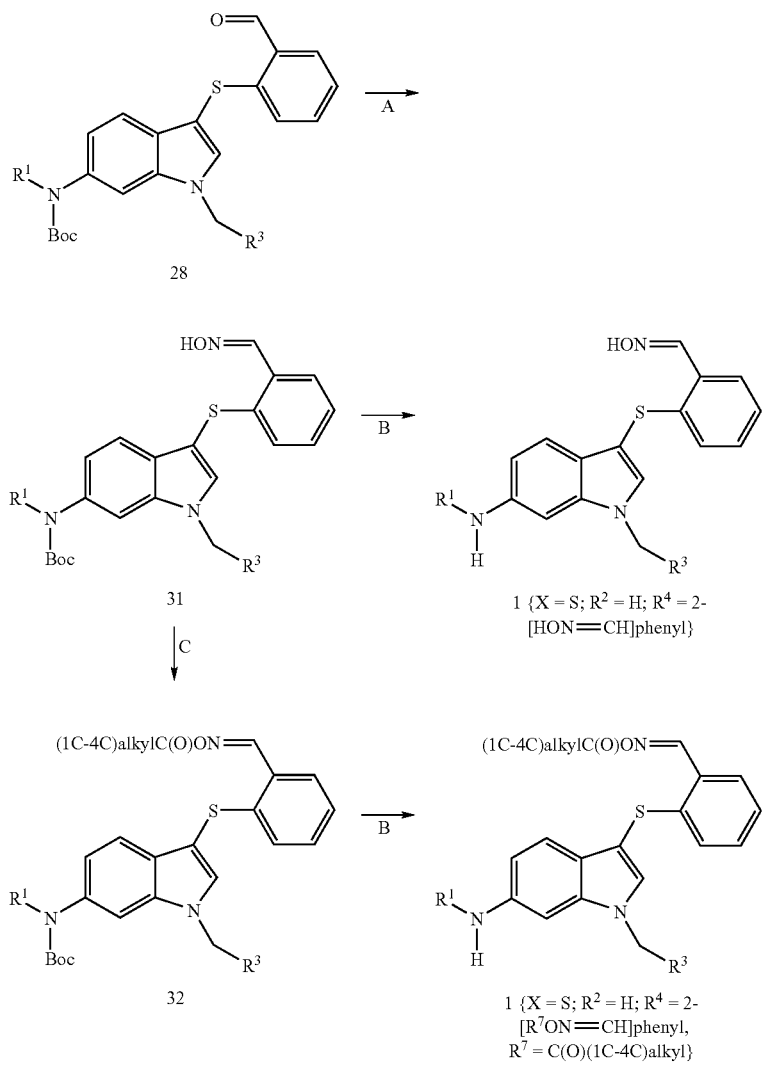

Conditions (reagents mentioned are examples only): A: Hydroxylamine hydrochloride. B: Deprotection. C: (1C4C)alkylC(O)Y (Y=Cl, or Br).

Scheme 6 gives another example of a synthesis route which allows preparation of compounds of the invention 1 with R⁴ is phenyl, or an aromatic 6-membered heterocycle, substituted at the ortho position with C(O)(1C-4C)alkyl, CO₂(1C-4C)alkyl or cyano. Key step in this procedure is the palladium-catalyzed reaction of bromo compounds 33 or 35.

Scheme 6. Variation of R⁴ (part 4).

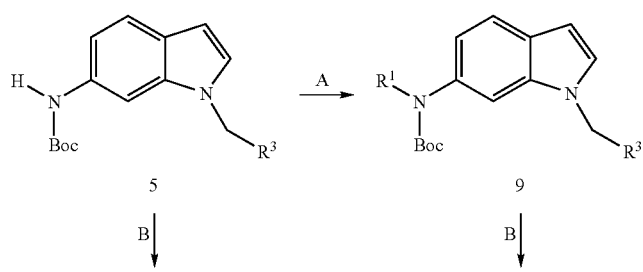

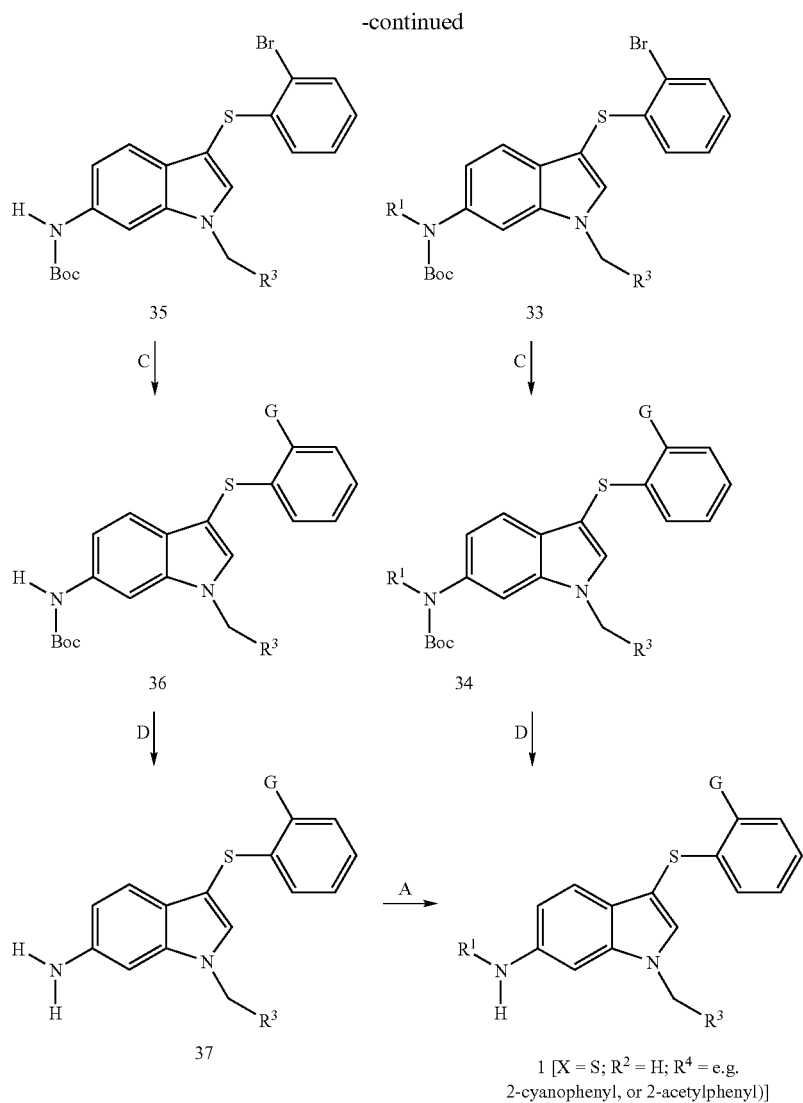

1 [X = S; R² = H; R⁴ = e.g. 2-cyanophenyl, or 2-acetylphenyl)]

Conditions (reagents mentioned are examples only): A: $R^1Y$ (Y=Cl, Br, p-toluenesulfonyloxy, or methanesulfonyloxy)/base. B: 2-Bromo-benzenethiol/sulfuryl chloride. C: Tetrakis(triphenylphosphine)-palladium(0)/zinc(II)cyanide [G=CN]; or 1) dichlorobis(triphenylphosphine)palladium (In)/(1-ethoxyvinyl)-tributyltin, 2) HCl [G is acetyl]; or palladium catalyst/carbon monoxide/(1C-4C)alkylOH [G=$CO_2$ (1C-4C)alkyl]. D: Trifluoroacetic acid.

Compounds of the invention wherein $R^8$, $R^9$, $R^{10}$ are independently (1C-2C)alkyl, fluoro or chloro can be prepared for instance from suitably substituted 6-nitroindole compounds. See for example for 4-methyl-6-nitroindole: WO 9218093, EP 460996; 4-chloro-6-nitroindole: U.S. Pat. No. 5,969,155.

Alternatively, compounds of the invention wherein $R^8$, $R^9$, $R^{10}$ are independently (1C-2C)alkyl, fluoro or chloro can be prepared from suitably substituted 6-aminoindole compounds. See for example for 6-amino-4-methylindole: WO 9218093, EP 460996; 6-amino-5-methylindole: WO 9218093, EP 460996; 6-amino-7-methylindole: WO 9823610; 6-amino-5-fluoroindole: WO 9218093; EP 460996; EP 409025, JP 63313770. The 4-, 5- or 7-substituted 6-aminoindoles can be processed to the compounds of the invention using standard methods. For instance, a suitably substituted 6-aminoindole compound can be converted, via selective protection of the 6-amino group, alkylation at the indole nitrogen, and deprotection of 6-amino, to compounds 4 of Scheme 1, which can then be processed further as described. Likewise, they might also be converted, via selective protection and deprotection, to compounds 12 of Scheme 2, which can then be processed further.

Alternatively, compounds of the invention wherein $R^8$, $R^9$, $R^{10}$ are independently (1C-2C)alkyl, fluoro or chloro can be prepared from suitably substituted 6-bromoindole compounds. See for example for 6-bromo-5-fluoroindole: US 2004224973, WO 2000012475; 6-bromo-5-methylindole: Dobbs, A. P. et al, Synlett (1999) (10) 1594-1596. The 4-, 5- or 7-substituted 6-bromoindoles can be converted to 4-, 5- or 7-substituted 6-aminoindoles via standard synthetic methodology, e.g. Buchwald chemistry, which then can be processed to compounds of the invention as described above.

The present invention is further described in the following examples which are not in any way intended to limit the scope of the invention as claimed.

EXAMPLES

Example 1

[1-(3,5-Difluoro-benzyl-3-(2-nitro-phenylsulfanyl)-1H-indol-6-yl]-methyl-amine i)—Sodium hydride (50% dispersion in oil, 4.8 g, 100 mmol) was added to a solution of 6-nitroindole (15.0 g, 92.6 mmol) in dry dimethylformamide (750 ml). After 30 min. stirring, 1-bromomethyl-3,5-difluoro-benzene (19.5 g, 94 mmol) was added. Stirring was continued for 1 h and the reaction mixture was quenched with water. The product was extracted into ethyl acetate; the combined organic phases were washed with brine, dried over sodium sulfate and concentrated under reduced pressure. The crude product was stirred with heptane to produce a white solid which was collected by filtration to give 1-(3,5-difluoro-benzyl)-6-nitro-1H-indole (33 g). The product was used in the following step without further purification.

ii)—A solution of the product obtained in the previous step (33 g) in a mixture of tetrahydrofuran (750 ml) and 2-propanol (750 ml), containing palladium on carbon (10%, 4.0 g) was stirred under hydrogen overnight. The mixture was filtered over celite and the filtrate was concentrated under reduced pressure, to give 1-(3,5-difluoro-benzyl)-1H-indol-6-ylamine (23 g). The product was used in the following step without further purification.

iii)—A solution of the product obtained in the previous step (23 g, 89.1 mmol) in a mixture of 1-methyl-2-pyrrolidinone (750 ml) and triethylamine (12.6 g, 125 mmol) was treated with di-tert-butyl dicarbonate (23.3 g, 107 mmol). The reaction mixture was stirred overnight and then quenched with a saturated aqueous solution of sodium hydrogencarbonate. The product was extracted into toluene; the combined organic phases were washed with water and brine, dried over sodium sulfate and concentrated under reduced pressure, to give [1-(3,5-difluoro-benzyl)-1H-indol-6-yl]-carbamic acid tert-butyl ester (16.5 g). The product was used in the following step without further purification.

iv)—2-Nitrobenzenesulfonyl chloride (8.7 g, 46 mmol) was added to a solution of the product obtained in the previous step (16.5 g, 46 mmol) in dichloromethane (500 ml). The reaction mixture was stirred for 1 h and then quenched with a saturated aqueous solution of sodium hydrogencarbonate. The product was extracted into ethyl acetate; the combined organic phases were washed with brine, dried over sodium sulfate and concentrated under reduced pressure, to give [1-(3,5-difluoro-benzyl)-3-(2-nitro-phenylsulfanyl)-1H-indol-6-yl]-carbamic acid tert-butyl ester (23.5 g). The product was used in the following step without further purification.

v)—A solution of the product obtained in the previous step (10 g, 19.5 mmol) in dimethyl formamide (100 ml) was added dropwise to a suspension of sodium hydride (60% dispersion in oil, 0.94 g, 23.5 mmol) in dimethyl formamide (60 ml), cooled to 0° C. After 30 min. stirring, iodomethane (1.34 ml, 21.5 mmol) was added and stirring was continued for 1 h. The mixture was quenched with water and the product was extracted into ethyl acetate. The combined organic phases were washed with water and brine, dried over sodium sulfate and concentrated under reduced pressure. Column chromatography (heptane/ethyl acetate 7:3) afforded [1-(3,5-difluoro-benzyl)-3-(2-nitro-phenylsulfanyl)-1H-indol-6-yl]-methyl-carbamic acid tert-butyl ester (6.9 g).

vi)—Trifluoroacetic acid (19.5 ml, 263 mmol) was added to a solution of the product obtained in the previous step (6.9 g, 13.1 mmol) in dichloromethane (200 ml), cooled to 0° C. The reaction mixture was stirred at room temperature for 3 h and then quenched with a saturated aqueous solution of sodium hydrogencarbonate and solid sodium hydrogencarbonate. The product was extracted into dichloromethane; the combined organic phases were washed with water and brine, dried over sodium sulfate and concentrated under reduced pressure. Column chromatography (heptane/ethyl acetate 7:3) afforded [1-(3,5-difluoro-benzyl)-3-(2-nitro-phenylsulfanyl)-1H-indol-6-yl]-methyl-amine (5.2 g). $^1$H-NMR (CDCl$_3$) δ 8.26 (dd, 1H, J=8.2 and 1.2 Hz), 7.28 (d, 1, J=8.2H), 7.28 (ddd, 1H, J=8.2, 7.4 and 1.2 Hz), 7.22 (s, 1H), 7.17 (ddd, 1H1, J=8.2, 7.4 and 1.2 Hz), 7.03 (dd, 1H, J=8.2 and 1.2 Hz), 6.74 (tt, 1H, J=8.2 and 2.3 Hz), 6.67 (m, 2H), 6.57 (dd, 1H, J=8.2 and 1.0 Hz), 6.37 (d, 1H, J=2.0 Hz), 5.28 (s, 2H), 3.83 (bs, 1H), 2.84 (s, 3H).

Example 2

Methyl-[3-(2-nitro-phenylsulfanyl)-1-pyridin-2-ylmethyl-1H-indol-6-yl]-amine i)—Sodium hydride (60% dispersion in oil, 15.5 g, 319 mmol) was added in portions to a solution of 6-nitroindole (23.5 g, 145 mmol) in 1-methyl-2-pyrrolidinone (1000 ml). After 45 min. stirring, 2-chloromethyl-pyridine hydrochloride (28.2 g, 174 mmol) was added in portions. Stirring was continued for 1 h and the reaction mixture was poured into a saturated aqueous solution of ammonium chloride. The product was extracted into ethyl acetate; the combined organic phases were washed with brine, dried over sodium sulfate and concentrated under reduced pressure. Column chromatography (heptane/ethyl acetate 1:1→ethyl acetate) afforded 6-nitro-1-pyridin-2-ylmethyl-1H-indole (30 g).

ii)—A solution of the product obtained in the previous step (28.0 g, 110.6 mmol) in ethanol (96%, 500 ml) was heated at 60° C. Concentrated hydrochloric acid (18.2 ml, 221.2 mmol) was added followed by tin(II) chloride dihydrate (133 g, 586.3 mmol). The reaction mixture was heated at 60° C. for 5 h. After cooling, it was quenched with a saturated aqueous solution of sodium hydrogencarbonate and solid sodium hydrogencarbonate and filtered. The filtrate was extracted with ethyl acetate; the combined organic phases were washed with brine, dried over sodium sulfate and concentrated under reduced pressure. Column chromatography (heptane/ethyl acetate 4:6→2:8) afforded 1-pyridin-2-ylmethyl-1H-indol-6-ylamine (19 g).

iii)—Following a procedure analogous to that described under iii of Example 1, the product obtained in the previous step (19 g, 85.2 mmol) was reacted with di-tert-butyl dicarbonate to give, after column chromatography (heptane/ethyl acetate 2:8, containing some triethylamine), (1-pyridin-2-ylmethyl-1H-indol-6-yl)-carbamic acid tert-butyl ester (22.5 g).

iv)—A solution of the product obtained in the previous step (22.5 g, 69.9 mmol) in dry diethyl ether (800 ml) was treated with 2-nitrobenzenesulfenyl chloride (13.3 g, 69.9 mmol). The reaction mixture was stirred at room temperature overnight and then poured into a saturated aqueous solution of sodium hydrogencarbonate. The product was extracted into ethyl acetate; the combined organic phases were washed with brine, dried over sodium sulfate and concentrated under reduced pressure. Column chromatography (heptane/ethyl acetate 1:1→3:7, containing some triethylamine) afforded [3-(2-nitro-phenylsulfanyl)-1-pyridin-2-ylmethyl-1H-indol-6-yl]-carbamic acid tert-butyl ester (23.6 g).

v)—Following a procedure analogous to that described under v of Example 1, the product obtained in the previous step (7.05 g, 14.8 mmol) was methylated giving, after column chromatography (heptane/ethyl acetate 6:4→1:1), methyl-[3-(2-nitro-phenylsulfanyl)-1-pyridin-2-ylmethyl-1H-indol-6-yl]-carbamic acid tert-butyl ester (6.94 g).

vi)—Following a procedure analogous to that described under vi of Example 1, the product obtained in the previous step (6.94 g, 14.2 mmol) was deprotected giving, after column chromatography (heptane/ethyl acetate 4:6), methyl-[3-(2-nitro-phenylsulfanyl)-1-pyridin-2-ylmethyl-1H-indol-6-yl]-amine (5.13 g). $^1$H-NMR (CDCl$_3$) δ 8.63 (dn, 1H, J=5.1 Hz), 8.26 (dd, 1H, J=8.4 and 1.4 Hz), 7.61 (td, 1H, J=7.8 and 2.0 Hz), 7.32 (s, 1H), 7.27 (d, 1H, J=8.6 Hz), 7.27 (m, 1H), 7.22 (ddd, 1H, J=7.8, 4.9 and 1.0 Hz), 7.16 (ddd, 1H, J=8.2, 7.4 and 1.6 Hz), 7.06 (dd, 1H, J=8.2 and 1.4 Hz), 6.86 (d, 1H, J=7.8 Hz), 6.55 (dd, 1H, J=8.6 and 2.0 Hz), 6.45 (d, 1H, J=2.0 Hz), 5.44 (s, 2H), 3.79 (bs, 1H), 2.82 (s, 3H).

Example 3

Methyl-[3-(2-nitro-phenylsulfanyl)-1-pyridine-3-ylmethyl-1H-indol-6-yl]-amine i)—Following a procedure analogous to that described under i of Example 2, 6-nitroindole (25 g, 154 mmol) was alkylated to produce, after column chromatography (heptane/ethyl acetate 1:1), 6-nitro-1-pyridin-3-ylmethyl-1H-indole (37.5 g). 3-Chloromethyl-pyridine hydrochloride was used as alkylating agent.

ii)—The product obtained in the previous step (20 g, 79 mmol) was dissolved in a mixture of ethanol (764 ml) and water (196 ml). Solid ammonium chloride (30 g, 553 mmol) and iron powder (325 mesh, 9 g, 158 mmol) were added and the reaction mixture was heated at 70° C. for 3 h. Additional portions of solid ammonium chloride (30 g, 553 mmol) and iron powder (325 mesh, 18 g, 316 mmol) were added and heating was continued overnight. The reaction mixture was cooled and filtered over dicalite; the residue was washed with ethanol. The filtrate was concentrated under reduced pressure and the residue was stirred with a mixture of water and ethylacetate. The product was extracted into ethyl acetate; the combined organic phases were washed with brine, dried over sodium sulfate and concentrated under reduced pressure. Column chromatography (ethyl acetate) afforded 1-pyridin-3-ylmethyl-1H-indol-6-ylamine (12.5 g).

iii)—Following a procedure analogous to that described under iii of Example 1, the product obtained in the previous step (12.5 g, 56.1 mmol) was reacted with di-tert-butyl dicarbonate to give, after column chromatography (heptane/ethyl acetate 1:1→ethyl acetate), (1-pyridin-3-ylmethyl-1H-indol-6-yl)-carbamic acid tert-butyl ester (11.0 g).

iv)—Following a procedure analogous to that described under iv of Example 2, the product obtained in the previous step (11.0 g, 34.1 mmol) was reacted with 2-nitrobenzenesulfenyl chloride to give, after column chromatography (ethyl acetate→ethyl acetate/methanol 8:2) [3-(2-nitro-phenylsulfanyl)-1-pyridin-3-ylmethyl-1H-indol-6-yl]-carbamic acid tert-butyl ester (15.0 g).

v)—Sodium hydride (60% dispersion in oil, 1.55 g, 38.8 mmol) was added in portions to a solution of the product obtained in the previous step (15.0 g, 31.5 mmol) in dry dimethyl formamide (278 ml), cooled to 0° C. After 30 min. stirring, iodomethane (2.1 ml, 33.7 mmol) was added. The reaction mixture was stirred at room temperature for 4 h and then poured into water. The product was extracted into ethyl acetate; the combined organic phases were washed with water and brine, dried over sodium sulfate and concentrated under reduced pressure. Column chromatography (toluene→toluene/acetone 8:2) afforded methyl-[3-(2-nitro-phenylsulfanyl)-1-pyridin-3-ylmethyl-1H-indol-6-yl]-carbamic acid tert-butyl ester (10.5 g).

vi)—Following a procedure analogous to that described under vi of Example 1, the product obtained in the previous step (10.5 g, 21.4 mmol) was deprotected to give, after column chromatography (toluene/acetone 8:2) methyl-[3-(2-nitro-phenylsulfanyl)-1-pyridin-3-ylmethyl-1H-indol-6-yl]-amine (5.8 g). $^1$H-NMR (CDCl$_3$) δ 8.59 (d, 1H, J=2.3 Hz), 8.57 (dd, 1H, J=5.1 and 1.8 Hz), 8.25 (dd, 1H, J=8.2 and 1.6 Hz), 7.44 (dt, 1H, J=8.2 and 1.9 Hz), 7.27 (m, 2H), 7.26 (d, 1H, J=8.6 Hz), 7.23 (s, 1H), 7.16 (ddd, 1H, J=8.2, 7.4 and 1.6 Hz), 7.03 (dd, 1H, J=8.2 and 1.4 Hz), 6.55 (dd, 1H, J=8.8 and 1.9 Hz), 6.42 (d, 1H, J=1.9 Hz), 5.33 (s, 2H), 3.82 (bs, 1H), 2.84 (s, 3H).

Example 4

Preparation of Synthetic Intermediate methyl-[3-(2-nitro-phenylsulfanyl)-1H-indol-6-yl]-carbamic acid tert-butyl ester i)—A solution of 6-nitroindole (25 g, 154 mmol) in dry tetrahydrofuran (900 ml) was cooled to −78° C. and treated with n-butyllithium (2.5 M solution in hexanes, 67.0 ml, 169 mmol). After 20 min. stirring, chloro-triisopropyl-silane (33.0 ml, 155 mmol) was added. The cooling bath was removed and the reaction mixture was stirred for 2 h. The mixture was quenched with water and the product was extracted into ethyl acetate. The combined organic phases were washed with brine, dried over sodium sulfate and concentrated under reduced pressure. Column chromatography (heptane/ethyl acetate 95:5) afforded 6-nitro-1-triisopropylsilanyl-1H-indole (41.5 g).

ii)—Following a procedure analogous to that described under ii of Example 3, the product obtained in the previous step (10 g, 31.5 mmol) was reduced with iron powder/ammonium chloride to produce, after column chromatography (heptane/ethyl acetate 9:1), 1-triisopropylsilanyl-1H-indol-6-ylamine (6.09 g).

iii)—A solution of the product obtained in the previous step (5.68 g, 19.7 mmol) in dichloromethane (29.5 ml), containing diisopropylethylamine (3.4 ml, 19.7 mmol), was cooled to 0° C. Ethyl chloroformate (1.89 ml, 19.7 mmol) was added slowly where after the reaction mixture was stirred at room temperature for 1.5 h. The reaction mixture was poured into water and the product was extracted into dichloromethane. The combined organic phases were washed with brine, dried over sodium sulfate and concentrated under reduced pressure, to give (1-triisopropylsilanyl-1H-indol-6-yl)-carbamic acid ethyl ester (7.58 g). The product was used in the following step without further purification.

iv)—A solution of the product obtained in the previous step (7.58 g) in dry tetrahydrofuran (48.8 ml), cooled to 0° C., was treated with lithium aluminium hydride (1 M solution in tetrahydrofuran, 39 ml, 39 mmol). The reaction mixture was stirred at room temperature for 2 h and at 40° C. for 2 h and then quenched with a saturated aqueous solution of sodium sulfate. The mixture was filtered over dicalite and the filtrate was concentrated under reduced pressure. Column chromatography (heptane/ethyl acetate 8:2) afforded methyl-(1-triisopropylsilanyl-1H-indol-6-yl)-amine (4.73 g).

v)—Following a procedure analogous to that described under iii of Example 1, the product obtained in the previous step (2.5 g, 8.28 mmol) was reacted with di-tert-butyl dicarbonate to give, after column chromatography (heptane/ethyl acetate 98:2), methyl-(1-triisopropylsilanyl-1H-indol-6-yl)-carbamic acid tert-butyl ester (3.06 g).

vi)—A solution of the product obtained in the previous step (3.5 g, 8.81 mmol) in dichloromethane (100 ml), containing pyridine (1.4 ml), was treated with 2-nitrobenzenesulfenyl chloride (1.67 g, 8.81 mmol). The reaction mixture was stirred at room temperature overnight and then quenched with a saturated aqueous solution of sodium hydrogencarbonate. The dichloromethane was partially removed and the product was extracted into ethyl acetate. The combined organic phases were washed with a saturated aqueous solution of sodium hydrogencarbonate and brine, dried over sodium sulfate and concentrated under reduced pressure to give methyl-[3-(2-nitro-phenylsulfanyl)-1-triisopropylsilanyl-1H-indol-6-yl]-carbamic acid tert-butyl ester (5.28 g). The product was used in the following step without further purification.

vii)—Tetrabutylammonium fluoride (1 M solution in tetrahydrofuran, 8.9 ml, 8.9 mmol) was added dropwise to a solution of the product obtained in the previous step (5.28 g) in dry tetrahydrofuran (28 ml). The reaction mixture was stirred at room temperature for 30 min. whereafter it was quenched with a saturated aqueous solution of sodium hydrogencarbonate. The product was extracted with ethyl acetate; the combined organic phases were washed with a saturated aqueous solution of sodium hydrogencarbonate and brine, dried over sodium sulfate and concentrated under reduced pressure. Column chromatography (heptane/ethyl acetate 8:2) afforded methyl-[3-(2-nitro-phenylsulfanyl)-1H-indol-6-yl]-carbamic acid tert-butyl ester (2.8 g). $^1$H-NMR (CDCl$_3$) δ 8.72 (bs, 1H), 8.27 (dd, 1H, J=8.5 and 1.5 Hz), 7.50 (d, 1H, J=2.5 Hz), 7.42 (d, 1H, J=8.5 Hz), 7.25 (ddd, 1H, J=8.0, 8.0 and 1.5 Hz), 7.17 (ddd, 1, J=7.0, 7.0 and 1.5 Hz), 7.05 (dd, 1H, J=8.5 and 2.0 Hz), 6.93 (dd, 1H, J=8.5 and 1.5 Hz), 3.32 (s, 3H), 1.48 (s, 9H).

Example 5

Using methyl-[3-(2-nitro-phenylsulfanyl)-1H-indol-6-yl]-carbamic acid tert-butyl ester (Example 4) as starting material, later on named the starting indole, the following products were prepared:

Example 5a

[1-Benzyl-3-(2-nitro-phenylsulfanyl)-1H-indol-6-yl]-methyl-amine i)—Sodium hydride (60% dispersion in oil, 0.0253 g, 0.63 mmol) was added to a solution of the starting indole (0.126 g, 0.316 mmol) in dry dimethyl formamide (1.0 ml), cooled to 0° C. After 30 min. stirring, bromomethyl-benzene (0.0454 ml, 0.38 mmol) was added. The reaction mixture was stirred at room temperature overnight and then quenched with a saturated aqueous solution of ammonium chloride. The product was extracted into ethyl acetate; the combined organic phases were washed with water and brine, dried over sodium sulfate and concentrated under reduced pressure. Column chromatography (heptane/ethyl acetate 7:3) afforded [1-benzyl-3-(2-nitro-phenylsulfanyl)-1H-indol-6-yl]-methyl-carbamic acid tert-butyl ester (0.146 g).

ii)—Following a procedure analogous to that described under vi of Example 1, the product obtained in the previous step (0.146 g, 0.30 mmol) was deprotected to give [1-benzyl-3-(2-nitro-phenylsulfanyl)-1H-indol-6-yl]-methyl-amine (0.088 g). $^1$H-NMR (CDCl$_3$) δ 8.25 (dd, 1H, J=8.4 and 1.6 Hz), 7.32 (td, 1H, J=8.2 and 5.9 Hz), 7.27 (d, 1H, J=8.2 Hz), 7.26 (m, 1H), 7.22 (s, 1H), 7.16 (ddd, 1H, =8.2, 7.4 and 1.6 Hz), 7.04 (dd, 1H, J=8.2 and 1.6 Hz), 6.99 (m, 2H), 6.86 (dt, 1H, J=9.4 and 2.0 Hz), 6.56 (dd, 1H, J=8.6 and 2.3 Hz), 6.42 (d, 1, J=2.0 Hz), 5.30 (s, 2H), 3.80 (bs, 1H), 2.83 (s, 3H).

Example 5b

[1-(2-Fluoro-benzyl-3-(2-nitro-phenylsulfanyl)-1H-indol-6-yl]-methyl-amine i)—Cesium carbonate (0.180 g, 0.551 mmol) was added to an ice-cooled solution of the starting indole (0.200 g, 0.501 mmol) in dry dimethyl formamide (2.5 ml). After 1 h stirring, 1-bromomethyl-2-fluoro-benzene (0.060 ml, 0.501 mmol) was added and the reaction mixture was stirred for 2 h. The mixture was quenched with a saturated aqueous solution of sodium hydrogencarbonate and the product was extracted with ethyl acetate. The combined organic phases were washed with brine, dried over sodium sulfate and concentrated under reduced pressure, to give [1-(2-fluoro-benzyl)-3-(2-nitro-phenylsulfanyl)-1H-indol-6-yl]-methyl-carbamic acid tert-butyl ester (0.305 g). The product was used in the following step without further purification.

ii)—Following a procedure analogous to that described under vi of Example 1, the product obtained in the previous step (0.100 g, 0.197 mmol) was deprotected giving, after column chromatography (heptane/ethyl acetate 8:2), [1-(2-fluoro-benzyl-3-(2-nitro-phenylsulfanyl)-1H -indol-6-yl]-methyl-amine (0.058 g). $^1$H-NMR (CDCl$_3$) δ 8.25 (dd, 1H, J=8.0 and 1.5 Hz), 7.22-7.34 (m, 4H), 6.99-7.17 (m, 5H), 6.55 (dd, 1H, J=8.5 and 2.0 Hz), 6.53 (d, 1H, J=2.0 Hz), 5.35 (s, 2H), 3.81 (bs, 1H), 2.87 (s, 3H).

Example 5c

[1-(3-Fluoro-benzyl)-3-(2-nitro-phenylsulfanyl)-1H-indol-6-yl]-methyl-amine

The title compound was prepared using procedures analogous to those described under Example 5a. 1-Bromomethyl-3-fluoro-benzene was used as alkylating agent.

$^1$H-NMR (CDCl$_3$) δ 8.24 (dd, 1H, J=8.4 and 1.4 Hz), 7.33 (m, 3H), 7.26 (d, 1H, J=8.6 Hz), 7.25 (m, 1H), 7.22 (s, 1H), 7.21 (m, 1H), 7.15 (ddd, 1H, J=8.2, 7.4 and 1.6 Hz), 7.04 (dd, 1H, J=8.2 and 1.6 Hz), 6.55 (dd, 1H, J=8.8 and 2.0 Hz), 6.47 (d, H, J=2.0 Hz), 5.30 (s, 2H), 3.79 (bs, 1H), 2.84 (s, 3H).

Example 5d

[1-(4-Fluoro-benzyl-3-(2-nitro-phenylsulfinyl)-1H-indol-6-yl]-methyl-amine

The title compound was prepared using procedures analogous to those described under Example 5b. 1-Bromomethyl-4-fluoro-benzene (1.5 equivalents) was used as alkylating agent.

$^1$H-NMR (CDCl$_3$) δ 8.25 (dd, 1H, J=8.0 and 1.5 Hz), 7.13-7.29 (m, 7H), 7.05 (d, 1H, J=7.5 Hz), 7.03 (dd, 1H, J=8.0 and 1.5 Hz), 6.55 (dd, 1H, J=8.5 and 2.0 Hz), 6.44 (d, 1H, J=2.0 Hz), 5.27 (s, 2H), 3.80 (bs, 1H), 2.84 (s, 3H).

Example 5e

Methyl-[3-(2-nitro-phenylsulfanyl)-1-pyridin-4-ylmethyl-1H-indol-6-yl]-amine

The title compound was prepared using procedures analogous to those described under Example 5b. The alkylation reaction was carried out using 2 equivalents of base; 4-chloromethyl-pyridine hydrochloride was used as alkylating agent. $^1$H-NMR (CDCl$_3$) δ 8.58 (m, 2H), 8.26 (dd, 1H, J=8.2 and 1.6 Hz), 7.28 (m, 1H), 7.28 (d, 1H, J=9.0 Hz), 7.24 (s, 1H), 7.17 (ddd, 1H, J=8.6, 7.4 and 1.6 Hz), 7.05 (m, 3H), 6.57 (dd, 1H, J=8.6, and 2.3 Hz), 6.33 (d, 1H, J=2.3 Hz), 5.33 (s, 2H), 3.83 (bs, 1H), 2.81 (s, 3H).

Example 5f

Methyl-[3-(2-nitro-phenylsulfanyl)-1-pyrimidin-2-ylmethyl-1H-indol-6-yl]-amine

The title compound was prepared using procedures analogous to those described under Example 5a. 2-Bromomethyl-pyrimidine (2.7 equivalents) was used as alkylating agent. $^1$H-NMR (CDCl$_3$) δ 8.72 (d, 2H, J=4.9 Hz), 8.24 (dd, 1H, J=8.2 and 1.6 Hz), 7.42 (s, 1H), 7.24 (m, 2H), 7.23 (d, 1H, J=8.2 Hz), 7.14 (ddd, 1H, J=8.6, 7.4 and 1.6 Hz), 7.08 (dd, 1H, J=8.2 and 1.6 Hz), 6.59 (d, 1H, J=2.0 Hz), 6.53 (dd, 1H, J=8.6 and 2.0 Hz), 5.50 (s, 2H), 3.80 (bs, 1H), 2.85 (s, 3H).

Example 5g

Methyl-[3-(2-nitro-phenylsulfanyl)-1-pyrimidin-5-ylmethyl-1H-indol-6-yl]-amine

The title compound was prepared using procedures analogous to those described under Example 5a. 5-Bromomethyl-pyrimidine was used as alkylating agent. $^1$H-NMR (CDCl$_3$) δ 9.19 (s, 1H), 8.61 (s, 2H), 8.26 (dd, 1H, J=8.2 and 1.6 Hz), 7.27 (m, 1H), 7.26 (d, 1H, J=8.6 Hz), 7.25 (s, 1H), 7.17 (ddd, 1H, J=8.6, 7.4 and 1.6 Hz), 7.01 (dd, 1H, J=8.2 and 1.6 Hz), 6.57 (dd, 1H, J=8.8 and 2.0 Hz), 6.38 (d, 1H, J=2.0 Hz), 5.35 (s, 2H), 3.87 (bs, 1H), 2.84 (s, 3H).

Example 5h

[1-Furan-2-ylmethyl-3-(2-nitro-phenylsulfanyl)-1H-indol-6-yl]-methyl-amine

The title compound was prepared using procedures analogous to those described under Example 5a. 2-Bromomethyl-furan (3 equivalents) was used as alkylating agent. $^1$H-NMR (CDCl$_3$) δ 8.24 (dd, 1H, J=8.5 and 1.5 Hz), 7.40 (d, 1H, J=2.0 Hz), 7.21-7.28 (m, 3H), 7.14 (dt, 1H, J=7.0 and 1.5 Hz), 7.02 (dd, 1H, J=8.5 and 1.5 Hz), 6.60 (d, 1H, J=2.0 Hz), 6.55 (dd, 1H, J=8.5 and 2.0 Hz), 6.36 (dd, 1H, J=3.5 and 2.0 Hz), 6.32 (d, 1H, J=2.5 Hz), 5.24 (s, 2H), 2.90 (s, 3H).

Example 5i

[1-Furan-3-ylmethyl-3-(2-nitro-phenylsulfanyl)-1H-indol-6-yl]-methyl-amine

The title compound was prepared using procedures analogous to those described under Example 5a. 3-Bromomethyl-furan (3 equivalents) was used as alkylating agent. $^1$H-NMR (CDCl$_3$) δ 8.24 (dd, 1H, J=8.2 and 1.6 Hz), 7.41 (s, 1H), 7.405 (s, 1H), 7.25 (d, 1H, J=9.0 Hz), 7.24 (m, 1H), 7.21 (s, 1H), 7.14 (ddd, 1H, J=8.6, 7.4 and 1.6 Hz), 7.01 (dd, 1H, J=8.2 and 1.6 Hz), 6.56 (m, 2H), 6.33 (t, 1H, J=1.2 Hz), 5.13 (s, 2H), 2.89 (s, 3H).

Example 5j

Methyl-[3-(2-nitro-phenylsulfanyl)-1-oxazol-4-ylmethyl-1H-indol-6-yl]-amine i)—A solution of oxazol-4-ylmethanol (0.200 g, 2.0 mmol) and triethylamine (0.326 ml, 2.3 mmol) in dimethyl formamide (6.0 ml), cooled to 0° C., was treated with methanesulfonyl chloride (0.178 ml, 2.3 mmol). After 1 h stirring, lithium bromide (0.486 g, 5.6 mmol) was added and stirring was continued for another 1 h. The reaction mixture was quenched with water and the product was extracted into ethyl acetate. The combined organic phases were washed with water, a saturated aqueous solution of sodium hydrogencarbonate and brine, dried over sodium sulfate and concentrated under reduced pressure, to give 4-bromomethyl-oxazole. The product was used immediately in the following step.

ii)—Following a procedure analogous to that described under i of Example 5a, the starting indole (0.40 g, 1.0 mmol) was alkylated with the bromide obtained in the previous step, to produce after column chromatography (heptane/ethyl acetate 6:4), methyl-[3-(2-nitro-phenylsulfanyl)-1-oxazol-4-ylmethyl-1H-indol-6-yl]-carbamic acid tert-butyl ester (0.355 g).

iii)—Following a procedure analogous to that described under vi of Example 1, the product obtained in the previous step (0.355 g, 0.74 mmol) was deprotected giving, after column chromatography (heptane/ethyl acetate 1:1), methyl-[3-(2-nitro-phenylsulfanyl-1-oxazol-4-ylmethyl-1H-indol-6-yl]-amine. (0.125 g). $^1$H-NMR (CDCl$_3$) δ 8.24 (dd, 1H, J=8.2 and 1.6 Hz), 7.90 (s, 1H), 7.49 (m, 1H), 7.28 (s, 1H), 7.24 (d, 1H, J=9.0 Hz), 7.24 (d, 1H), 7.14 (ddd, 1H, J=8.6, 7.4 and 1.6 Hz), 7.02 (dd, 1H, J=8.2 and 1.6 Hz), 6.55 (m, 2H), 5.25 (d, 2H, J=0.8 Hz), 3.85 (bs, 1H), 2.89 (s, 3H).

Example 5k

[1-Isoxazol-3-ylmethyl-3-(2-nitro-phenylsulfanyl)-1H-indol-6-yl]-methyl-amine

The title compound was prepared using procedures analogous to those described under Example 5a. 3-Bromomethyl-isoxazole was used as alkylating agent. $^1$H-NMR (CDCl$_3$) δ 8.37 (d, 1H, J=2.0 Hz), 8.25 (dd, 1, J=8.2 and 1.6 Hz), 7.27 (s, 1H), 7.25 (m, 1H), 7.24 (d, 1H, J=9.8 Hz), 7.16 (ddd, 1H, J=8.6, 7.4 and 1.6 Hz), 7.00 (dd, 1H, J=8.2 and 1.4 Hz), 6.55 (dd, 1H, J=8.6 and 2.0 Hz), 6.54 (s, 1H), 6.15 (d, 1H, J=1.6 Hz), 5.40 (s, 2H), 3.85 (bs, 1H), 2.88 (s, 3H).

Example 5l

Methyl-[3-(2-nitro-phenylsulfanyl)-1-thiazol-4-ylmethyl-1H-indol-6-yl]-amine i)—Cesium carbonate (0.326 g, 1.0 mmol) was added to an ice-cooled solution of the starting indole (0.200 g, 0.501 mmol) in dry 1-methyl-2-pyrrolidinone (2.5 ml). After 30 min. stirring, 4-chloromethyl-thiazole hydrochloride (0.0852 g, 0.501 mmol) was added and the reaction mixture was stirred at room temperature overnight. The mixture was quenched with a saturated aqueous solution of ammonium chloride and the product was extracted with ethyl acetate. The combined organic phases were washed with brine, dried over sodium sulfate and concentrated under reduced pressure. Column chromatography (heptane/ethyl acetate 1:1) afforded methyl-[3-(2-nitro-phenylsulfanyl)-1-thiazol-4-ylmethyl-1H-indol-6-yl]-carbamic acid tert-butyl ester (0.210 g).

ii)—Following a procedure analogous to that described under vi of Example 1, the product obtained in the previous step (0.210 g, 0.423 mmol) was deprotected giving, after column chromatography (toluene/acetone 9:1), methyl-[3-(2-nitro-phenylsulfanyl)-1-thiazol-4-ylmethyl-1H-indol-6-yl]-amine (0.137 g). $^1$H-NMR (CDCl$_3$) δ 8.84 (d, 1H, J=2.3 Hz), 8.25 (dd, 1H, J=8.2 and 1.6 Hz), 7.30 (s, 1H), 7.25 (m, 1H), 7.25 (d, 1H, J=7.8 Hz), 7.15 (ddd, 1H, J=8.2, 7.4 and 1.6 Hz), 7.04 (dd, 1H, J=8.2 and 1.6 Hz), 6.96 (m, 1H), 6.55 (dd, 1H, J=8.6 and 2.0 Hz), 6.52 (d, 1H, J=2.0 Hz), 3.83 (bs, 1H), 2.86 (s, 3H), 5.49 (d, 2H, J=0.6 Hz).

Example 5m

Methyl-[3-(2-nitro-phenylsulfanyl)-1-oxazol-2-ylmethyl-1H-indol-6-yl]-amine i)—n-Butyl lithium (1.6 M in hexane, 9.06 ml, 14.5 mmol) was added dropwise to a solution of oxazole (1.0 g, 14.5 mmol) in dry tetrahydrofuran (48 ml) at −78° C. After stirring for 30 min, dimethylformamide (11.2 ml, 145 mmol) was added and the reaction mixture was allowed to warm to room temperature. The mixture was stirred at room temperature for 4 h, quenched with water and acidified with hydrochloric acid (2 M). The water layer was extracted using ethyl acetate; the combined organic phases were washed with water and brine, dried over sodium sulfate and concentrated under reduced pressure, to give oxazole-2-carbaldehyde. The product was used immediately in the following step.

ii)—The product of the previous step (0.417 g, 4.3 mmol) in diethyl ether (3.6 ml) was added to a suspension of lithium aluminiumhydride (0.103 g, 4.3 mmol) in diethyl ether (7.4 ml). The reaction mixture was stirred overnight, quenched with a saturated aqueous solution of sodium sulfate and filtered over dicalite. The filtrate was dried over sodium sulfate and concentrated under reduced pressure, to give oxazol-2-yl-methanol.

iii)—Following a procedure analogous to that described under i of Example 5j, the crude product obtained in the previous step (0.100 g, 1.01 mmol) was treated with methanesulfonyl chloride and lithium bromide giving 2-bromomethyloxazole, which was used immediately in the following step.

iv)—Following a procedure analogous to that described under i of Example 5a, the starting indole (0.200 g, 0.50 mmol) was alkylated with the bromide obtained in the previous step (1 mmol) using sodium hydride (0.022 g, 0.55 mmol) as base. Column chromatography (heptane/ethyl acetate 8/2→1/1) gave methyl-[3-(2-nitro-phenylsulfanyl)-1-oxazol-2-ylmethyl-1H-indol-6-yl]-carbamic acid tert-butyl ester (0.113 g).

v)—Following a procedure analogous to that described under vi of Example 1, the product obtained in the previous step (0.050 g, 0.104 mmol) was deprotected giving, after column chromatography (heptane/ethyl acetate 6/4→1/1), methyl-[3-(2-nitro-phenylsulfanyl)-1-oxazol-2-ylmethyl-1H-indol-6-yl]-amine (0.033 g). $^1$H-NMR (DMSO) δ 8.24 (dd, 1H, J=8.3 and 1.3 Hz), 8.10 (d, 1H, J=0.7 Hz), 7.64 (s, 1H), 7.48 (ddd, 1H, J=8.3, 7.2 and 1.3 Hz), 7.32 (ddd, 1H, J=8.3, 7.2 and 1.2 Hz), 7.22 (d, 1H, J=0.7 Hz), 7.00 (d, 1H, J=8.5 Hz), 6.92 (dd, 1H, J=8.3 and 1.2 Hz), 6.56 (d, 1H, J=1.7 Hz), 6.49 (dd, 1H, J=8.5 and 1.7 Hz), 5.68 (q, 1H, J=5.0 Hz), 5.60 (s, 2H), 2.68 (d, 3H, J=5.2 Hz).

Example 5n

[1-Isoxazol-5-ylmethyl-3-(2-nitro-phenylsulfanyl)-1H-indol-6-yl]-methyl-amine i)—Isoxazole-5-carboxylic acid (0.500 g, 4.4 mmol) was dissolved in a solution of hydrochloric acid in ethanol (5 M) and refluxed for 5 hours. The mixture was concentrated under reduced pressure giving isoxazole-5-carboxylic acid ethyl ester, which was used immediately in the following step.

ii)—The product obtained in the previous step (0.450 g, 3.19 mmol) in diethyl ether was added dropwise to a suspension of lithium aluminiumhydride (0.121 g, 3.2 mmol) in diethyl ether (5.5 ml) at 0° C. After stirring at room temperature and reflux temperature for 4 h, the reaction mixture was quenched with a saturated aqueous solution of sodium sulfate and filtered over dicalite. The filtrate was concentrated under reduced pressure to give a mixture of starting material and product. The procedure described above was repeated to complete the reaction, to give isoxazol-5-yl-methanol (0.300 g).

iii)—Following a procedure analogous to that described under i of Example 5j, the crude product obtained in the previous step (0.200 g, 2.0 mmol) was treated with methanesulfonyl chloride and lithium bromide giving 5-bromomethyl-isoxazole, which was used immediately in the following step.

iv)—Following a procedure analogous to that described under i of Example 5a, the starting indole (0.400 g, 1.0 mmol) was alkylated with the bromide obtained in the previous step (2 mmol) using sodium hydride (0.044 g, 1.1 mmol) as base. Column chromatography (heptane/ethyl acetate 7:3) afforded [1-isoxazol-5-ylmethyl-3-(2-nitro-phenylsulfanyl)-1H-indol-6-yl]-methyl-carbamic acid tert-butyl ester (0.145 g).

v)—Following a procedure analogous to that described under vi of Example 1, the product obtained in the previous step (0.145 g, 0.30 mmol) was deprotected giving, after column chromatography (heptane/ethyl acetate 7:3→6:4), [1-isoxazol-5-ylmethyl-3-(2-nitro-phenylsulfanyl-1H-indol-6-yl]-methyl-amine (0.099 g). $^1$H-NMR (DMSO) δ 8.53 (d, 1H, J=1.7 Hz), 8.24 (dd, 1H, J=8.3 and 1.3 Hz), 7.65 (s, 1H), 7.48 (ddd, 1H, J=8.3, 7.2 and 1.3 Hz), 7.32 (ddd, 1H, J=8.3, 7.2 and 1.2 Hz), 7.01 (d, 1H, J=8.6 Hz), 6.91 (dd, 1H, J=8.3 and 1.2 Hz), 6.61 (d, 1H, J=1.7 Hz), 6.50 (dd, 1H, J=8.6 and 1.7 Hz), 6.43 (d, 1H, J=1.7 Hz), 5.68 (q, 1H, J=5.0 Hz), 5.66 (s, 2H), 2.70 (d, 3, J=5.0 Hz).

Example 5o

Methyl-[1-(3-meth 1-benzyl-3-(2-nitro-phenylsulfanyl)-1H-indol-6-yl]-amine i)—Following a procedure analogous to that described under i of Example 5a, the starting indole (0.100 g, 0.25 mmol) was alkylated with 3-methylbenzylbromide (0.038 ml, 0.28 mmol) using sodium hydride (0.011 g, 0.28 mmol) as base, to give methyl-[1-(3-methyl-benzyl)-3-(2-nitro-phenylsulfanyl)-1H-indol-6-yl]-carbamic acid tert-butyl ester. The product was used immediately in the following step.

ii)—Following a procedure analogous to that described under vi of Example 1, the product obtained in the previous step (0.25 mmol) was deprotected giving, after column chromatography (heptane/ethyl acetate 75:25), methyl-[1-(3-methyl-benzyl-3-(2-nitro-1-phenylsulfanyl-1H-indol-6-yl]-amine (0.070 g). $^1$H-NMR (CDCl$_3$) δ 8.24 (dd, 1H, J=8.2 and 1.2 Hz), 7.21-7.28 (m, 3H), 7.21 (s, 1H), 7.15 (ddd, 1H, J=8.2, 7.2 and 1.2 Hz) 7.09-7.12 (m, 1H), 7.04 (dd, 1H, J=8.2 and 1.2

Hz), 6.98-7.02 (m, 2H), 6.55 (dd, 1H, J=8.5 and 2.0 Hz), 6.50 (d, 1H, J=2.0 Hz), 5.26 (s, 2H), 3.80 (bs, 1H), 2.85 (s, 3H), 2.33 (s, 3H).

Example 5p

[1-(3-Chloro-benzyl)-3-(2-nitro-phenylsulfanyl)-1H-indol-6-yl]-methyl-amine i)—Following a procedure analogous to that described under i of Example 5a, the starting indole (100 mg, 0.25 mmol) was alkylated with 3-chlorobenzylbromide (0.037 ml, 0.28 mmol) using sodium hydride (0.011 g, 0.28 mmol) as base. After column chromatography (heptane/ethyl acetate 7:3), [1-(3-chloro-benzyl)-3-(2-nitro-phenylsulfanyl)-1H-indol-6-yl]-methyl-carbamic acid tert-butyl ester (0.045 g) was obtained.

ii)—Following a procedure analogous to that described under vi of Example 1, the product obtained in the previous step (0.045 g, 0.086 mmol) was deprotected giving, after column chromatography (heptane/ethyl acetate 7:3), [1-(3-chloro-benzyl-3-(2-nitro-phenylsulfanyl-1H -indol-6-yl]-meth 1-amine (0.024 g). $^1$H-NMR (DMSO) δ 8.25 (dd, 1H, J=8.3 and 1.2 Hz), 7.22 (s, 1H), 7.48 (ddd, 1H, J=8.3, 7.2 and 1.2 Hz), 7.30-7.42 (m, 4H), 7.22 (dt, 1H, J=7.5 and 1.3 Hz), 7.03 (d, 1H, J=8.5 Hz), 6.91 (dd, 1H, J=8.3 and 1.0 Hz), 6.53 (d, 1H, J=1.6 Hz), 6.49 (dd, 1H, J=8.5 and 1.6 Hz), 5.65 (q, 1H, J=5.0 Hz), 5.43 (s, 2H), 2.66 (d, 3H, J=5.0 Hz).

Example 5q

Methyl-[3-(2-nitro-phenylsulfanyl)-1-(3-trifluoromethyl-benzyl)-1H-indol-6-yl]-amine i)—Following a procedure analogous to that described under i of Example 5a, the starting indole (0.100 g, 0.25 mmol) was alkylated with 1-bromomethyl-3-trifluoromethyl-benzene (0.043 ml, 0.28 mmol) using sodium hydride (0.011 g, 0.28 mmol) as base. Column chromatography (heptane/ethyl acetate 7:3) afforded methyl-[3-(2-nitro-phenylsulfanyl)-1-(3-trifluoromethyl-benzyl)-1H-indol-6-yl]-carbamic acid tert-butyl ester (0.099 g).

ii)—Following a procedure analogous to that described under vi of Example 1, the product obtained in the previous step (0.099 g, 0.18 mmol) was deprotected giving, after column chromatography (heptane/ethyl acetate 7:3), methyl-[3-(2-nitro-phenylsulfanyl)-1-(3-trifluoromethyl-benzyl)-1H-indol-6-yl]-amine (0.068 g). $^1$H-NMR (CDCl$_3$) δ 8.25 (dd, A, J=8.2 and 1.5 Hz), 7.55-7.59 (d, 1H), 7.44-7.49 (m, 2H), 7.30-7.34 (i, 1H), 7.24-7.29 (m, 2H), 7.23 (s, 1H), 7.16 (ddd, 1H, J=8.2, 7.2 and 1.2 Hz), 7.02 (dd, 1H, J=8.2 and 1.2 Hz), 6.56 (dd, 1H, J=8.5 and 1.2 Hz), 6.41 (d, 1H, J=2.0 Hz), 5.36 (s, 2H), 3.82 (bs, 1H), 2.83 (s, 3H).

Example 5r

3-[6-Methylamino-3-(2-nitro-phenylsulfanyl)-1-indol-1-ylmethyl]-benzonitrile

The title compound was prepared using procedures analogous to those described under Example 5b 3-Bromomethyl-benzonitrile was used as alkylating agent. $^1$H-NMR (CDCl$_3$) δ 8.26 (dd, 1H, J=8.3 and 1.5 Hz), 7.61 (dt, 1H, J=7.7 and 1.3 Hz), 7.47 (t, 1H, J=7.7 Hz), 7.44 (bs, 1H), 7.38 (bd, 1, J=7.7 Hz), 7.27-7.32 (m, 2H), 7.22 (s, 1H), 7.17 (ddd, 1H, J=8.3, 7.1 and 1.3 Hz), 7.03 (dd, 1H, J=8.2 and 1.3 Hz), 6.57 (dd, 1H, J=8.7 and 1.8 Hz), 6.36 (d, 1H, J=1.8 Hz), 5.35 (s, 2H), 3.84 (bs, 1H), 2.83 (s, 3H).

Example 5s

5-[6-Methylamino-3-(2-nitro-phenylsulfanyl)-indol-1-ylmethyl]-isophthalonitrile

The title compound was prepared using procedures analogous to those described under Example 5b. 5-Bromomethyl-isophthalonitrile (see Fisher, T.; Dershem, S.; Prewitt, M.; *J. Org. Chem.*; 55; 3; 1990, pages 1040-1043) was used as alkylating agent. $^1$H-NMR (CDCl$_3$) δ 8.26 (dd, 1H, J=8.4 and 1.3 Hz), 7.88 (t, 1H, J=1.3 Hz), 7.59 (d, 2H, J=1.3 Hz), 7.32 (ddd, 1H, J=8.4, 7.2 and 1.3 Hz), 7.31 (d, 1H, J=8.6 Hz), 7.21 (s, 1H), 7.19 (ddd, 1H, J=8.4, 7.2 and 1.3 Hz), 7.01 (dd, 1H, J=8.4 and 1.3 Hz), 6.60 (dd, 1H, J=8.6 and 1.9 Hz), 6.27 (d, 1H, J=1.9 Hz), 5.40 (s, 2H), 3.89 (bs, 1H), 2.84 (s, 3H).

Example 6

2-[1-(3,5-Difluoro-benzyl-6-methylamino-1H-indol-3-ylsulfanyl]-benzonitrile

Method 1 i)—Following a procedure analogous to that described under step v of Example 1, [1-(3,5-difluoro-benzyl)-1H-indol-6-yl]-carbamic acid tert-butyl ester (Example 1, step iii; 1.0 g, 2.79 mmol) was methylated to give, after column chromatography (heptane→heptane/ethyl acetate 8:2), [1-(3,5-difluoro-benzyl)-1H-indol-6-yl]-methyl-carbamic acid tert-butyl ester (1.01 g).

ii)—A solution of 2-mercapto-benzoic acid methyl ester (0.186 ml, 1.35 mmol) in dichloromethane (10 ml) was cooled to 0° C. and chlorine gas was passed through the solution for 2 min. The mixture was stirred at room temperature for 15 min.; nitrogen was passed through and the mixture was concentrated under reduced pressure. A solution of the product obtained in the previous step (0.50 g, 1.35 mmol) in dichloromethane (10 ml) was added to the freshly prepared sulfenyl chloride and the reaction mixture was stirred at room temperature overnight. The mixture was poured into a saturated aqueous solution of sodium hydrogencarbonate and the product was extracted into ethyl acetate. The combined organic phases were washed with brine, dried over sodium sulfate and concentrated under reduced pressure. Column chromatography afforded 2-[6-(tert-butoxycarbonyl-methyl-amino)-1-(3,5-difluoro-benzyl)-1H-indol-3-ylsulfanyl]-benzoic acid methyl ester (0.644 g).

iii)—A solution of lithium hydroxide monohydrate (0.322 g, 7.7 mmol) in water (25 ml) was added to a solution of the product obtained in the previous step (0.544 g, 1.01 mmol) in tetrahydrofuran (25 ml). The reaction mixture was heated at 60° C. overnight, cooled and then neutralized with an aqueous solution of citric acid (3%). The product was extracted into ethyl acetate; the combined organic phases were washed with brine, dried over sodium sulfate and concentrated under reduced pressure. Column chromatography (heptane→heptane/ethyl acetate 1:1) afforded 2-[6-(tert-butoxycarbonyl-methyl-amino)-1-(3,5-difluoro-benzyl)-1H-indol-3-ylsulfanyl]-benzoic acid (0.195 g).

iv)—A suspension of the product obtained in the previous step (0.195 g, 0.37 mmol) in dichloromethane (20 ml) was treated with 2-(1H-benzotriazol-1-yl)-1,1,3,3-tetramethyluronium tetrafluoroborate (0.179 g, 0.56 mmol), solid ammonium chloride (0.060 g, 1.12 mmol), and diisopropylethylamine (0.195 ml, 1.12 mmol) and the reaction mixture was stirred at room temperature overnight. The mixture was poured into a saturated aqueous solution of sodium hydrogencarbonate and the product was extracted into ethyl acetate. The combined organic phases were washed with brine, dried over sodium sulfate and concentrated under reduced pressure. Column chromatography (heptane→heptane/ethyl acetate 3:7) afforded [3-(2-carbamoyl-phenylsulfanyl)-1-(3,5-difluoro-benzyl)-1H-indol-6-yl]-methyl-carbamic acid tert-butyl ester (0.144 g).

v)—A ice-cooled solution of the product obtained in the previous step (0.144 g, 0.28 mmol) in dichloromethane (5 ml), containing triethylamine (0.147 ml, 1.05 mmol), was treated with trifluoromethanesulfonic anhydride (0.093 ml, 0.55 mmol). The reaction mixture was stirred at 0° C. for 2 h and then at room temperature overnight. The mixture was poured into a saturated aqueous solution of sodium hydrogencarbonate and the product was extracted into ethyl acetate. The combined organic phases were washed with brine, dried over sodium sulfate and concentrated under reduced pressure. Column chromatography (heptane→heptane/ethyl acetate 3:7) afforded [3-(2-cyano-phenylsulfanyl)-1-(3,5-difluoro-benzyl)-1H-indol-6-yl]-methyl-carbamic acid tert-butyl ester (0.061 g).

vi)—Following a procedure analogous to that described under step vi of Example 1, the product obtained in the previous step (0.061 g, 0.12 mmol) was deprotected to give, after column chromatography (heptane→heptane/ethyl acetate 6:4), 2-[1-(3,5-difluorobenzyl)-6-methylamino-1H-indol-3-ylsulfanyl]-benzonitrile (0.026 g). $^1$H-NMR (CDCl$_3$) δ 7.57 (dd, 1H, J=7.5 and 1.5 Hz), 7.34 (d, 1H, J=8.5 Hz), 7.22-7.29 (m, 2H), 7.11 (dt, 1H, J=8.0 and 1.5 Hz), 6.92 (d, 1H, J=8.5 Hz), 6.74 (tt, 1H, J=8.5 and 2.5 Hz), 6.67 (bd, 2H, J=8.0 Hz), 6.58 (dd, 1H, =8.5 and 2.0 Hz), 6.35 (d, H, J=2.0 Hz), 5.27 (s, 2H), 3.81 (bs, 1H), 2.83 (d, 3H).

Method 2 i)—Sulfuryl chloride (1.08 ml, 13.4 mmol) was added to a solution of 2-bromobenzenethiol (1.27 g, 6.69 mmol) in dichloromethane (45 ml). The reaction mixture was stirred at room temperature for 15 min. and concentrated under reduced pressure. The resulting material was dissolved in diethyl ether and added dropwise to a solution of [1-(3,5-difluoro-benzyl)-1H-indol-6-yl]-methyl-carbamic acid tert-butyl ester (Example 6, method 1, step i; 2.50 g, 6.71 mmol) in diethyl ether (45 ml). The reaction mixture was stirred for 3.5 h and then poured into a saturated aqueous solution of sodium hydrogencarbonate. The product was extracted into ethyl acetate; the combined organic phases were washed with brine, dried over sodium sulfate and concentrated under reduced pressure. Column chromatography (heptane/ethyl acetate 9:1→8:2) afforded [3-(2-bromo-phenylsulfanyl)-1-(3,5-difluoro-benzyl)-1H-indol-6-yl]-methyl-carbamic acid tert-butyl ester (3.02 g).

ii)—A mixture of the product obtained in the previous step (0.851 g, 1.52 mmol), zinc (II) cyanide (0.214 g, 1.83 mmol) and tetrakis(triphenylphosphine)palladium(0) (0.053 g, 0.0456 mmol) in dimethylformamide (15 ml) was heated in a microwave apparatus (175 W, 150° C.) for 8 min. The reaction mixture was quenched with water. The product was extracted into ethyl acetate; the combined organic phases were washed with water and brine, dried over sodium sulfate and concentrated under reduced pressure. Column chromatography (heptane/ethyl acetate 95:5→6:4) afforded [3-(2-cyano-phenylsulfanyl)-1-(3,5-difluoro-benzyl)-1H-indol-6-yl]-methyl-carbamic acid tert-butyl ester (0.827 g).

iii)—Following a procedure analogous to that described under step vi of Example 1, the product obtained in the previous step (0.825 g, 1.63 mmol) was deprotected to give, after column chromatography (heptane/ethyl acetate 85:15→8:2) and freeze-drying (dioxane), the title compound (0.388 g).

Example 7

2-(6-Methylamino-1-pyridin-2-ylmethyl-1H-indol-3-ylsulfanyl)-benzonitrile i)—Following a procedure analogous to that described under step i of Example 6, method 2, (1-pyridin-2-ylmethyl-1H-indol-6-yl)-carbamic acid tert-butyl ester (Example 2, step iii, 1.44 g, 3.10 mmol) was reacted with 2-mercapto-benzoic acid methyl ester/sulfuryl chloride to give, after column chromatography (heptane/ethyl acetate 1:1), 2-(6-tert-butoxycarbonylamino-1-pyridin-2-ylmethyl-1H-indol-3-ylsulfanyl)-benzoic acid methyl ester (0.947 g).

ii)—Following a procedure analogous to that described under step iii of Example 6, method 1, the product obtained in the previous step (0.847 g, 1.73 mmol) was saponified to give 2-(6-tert-butoxycarbonylamino-1-pyridin-2-ylmethyl-1H-indol-3-ylsulfanyl)-benzoic acid (0.847 g).

iii)—Following a procedure analogous to that described under step iv of Example 6, method 1, the product obtained in the previous step (0.847 g, 1.78 mmol) was converted to the amide, to give, after column chromatography (dichloromethane/methanol 9:1), [3-(2-carbamoyl-phenylsulfanyl)-1-pyridin-2-ylmethyl-1H-indol-6-yl]-carbamic acid tert-butyl ester (0.615 g).

iv)—Following a procedure analogous to that described under step v of Example 6, method 1, the product obtained in the previous step (0.513 g, 1.08 mmol) was converted to the cyano compound to give, after column chromatography (dichloromethane/methanol 9:1), [3-(2-cyano-phenylsulfanyl)-1-pyridin-2-ylmethyl-1H-indol-6-yl]-carbamic acid tert-butyl ester (0.150 g).

v)—Following a procedure analogous to that described under step i of Example 2, the product obtained in the previous step (0.150 g, 0.33 mmol) was methylated to give, after column chromatography (toluene/acetone 8:2), [3-(2-cyano-phenylsulfanyl)-1-pyridin-2-ylmethyl-1H-indol-6-yl]-methyl-carbamic acid tert-butyl ester (0.044 g).

vi)—Following a procedure analogous to that described under step vi of Example 1, the product obtained in the previous step (0.044 g, 0.090 mmol) was deprotected to give, after column chromatography (toluene/acetone 8:2) and freeze-drying (acetonitrile), 2-(6-methylamino-1-pyridin-2-ylmethyl-1H-indol-3-ylsulfanyl)-benzonitrile (0.018 g). $^1$H-NMR (CDCl$_3$) δ 8.62 (bs, 1H), 7.61 (dd, 1H, J=7.5 and 1.5 Hz), 7.57 (dd, 1H, J=7.5 and 1.5 Hz), 7.34 (d, 1H, J=8.5 Hz), 7.33 (s, 1H), 7.18-7.33 (m, 2H), 7.10 (dt, 1H, J=7.5 and 1.0 Hz), 6.94 (d, 1H, J=7.5 Hz), 6.85 (d, 1H, J=8.0 Hz) 6.56 (dd, 1H, J=8.5 and 2.0 Hz), 6.43 (d, 1H, J=1.5 Hz), 5.43 (s, 2H), 2.81 (s, 3H).

Example 8

1-{2-[1-(3,5-Difluoro-benzyl)-6-methylamino-1H-indol-3-ylsulfanyl]-phenyl}-ethanone i)—A solution of [3-(2-bromo-phenylsulfanyl)-1-(3,5-difluoro-benzyl)-1H-indol-6-yl]-methyl-carbamic acid tert-butyl ester (Example 6, method 2, step i; 1.00 g, 1.79 mmol) in toluene (oxygen-free, 25 ml), containing dichlorobis(triphenylphosphine)palladium(II) (0.076 g, 0.0672 mmol) and (1-ethoxyvinyl)tributyltin (0.824 ml, 2.44 mmol) was heated under reflux overnight. After cooling, hydrochloric acid (2M, 15 ml) was added and the mixture was stirred for 1 h. The mixture was quenched with a saturated aqueous solution of sodium hydrogencarbonate and the product was extracted into ethyl acetate. The combined organic phases were washed with brine, dried over sodium sulfate and concentrated under reduced pressure. Column chromatography (heptane/ethyl acetate 9:1→85:15) afforded [3-(2-acetyl-phenylsulfanyl)-1-(3,5-difluoro-benzyl)-1H-indol-6-yl]-methyl-carbamic acid tert-butyl ester (0.245 g).

ii)—A suspension of the product obtained in the previous step (0.050 g, 0.096 mmol) in a mixture of anisol (0.5 ml) and dichloromethane (1 ml), cooled to 0° C., was treated with trifluoroacetic acid (0.5 ml). The reaction mixture was stirred for 1 h and then poured into a saturated aqueous solution of sodium hydrogencarbonate. The product was extracted into ethyl acetate; the combined organic phases were washed with brine, dried over sodium sulfate and concentrated under reduced pressure. HPLC (acetonitrile/water 4:6→9:1) afforded 1-{2-[1-(3,5-difluoro-benzyl)-6-methylamino-1H-indol-3-ylsulfanyl]-phenyl}-ethanone (0.010 g). $^1$H-NMR (CDCl$_3$) δ 7.30 (d, 11, J=8.5 Hz), 7.14-7.21 (m, 3H), 7.11 (dt, 1H, J=7.5 and 1.0 Hz), 6.99 (dd, 1H, J=8.0 and 1.0 Hz), 6.72 (tt, 1H, J=8.5 and 2.5 Hz), 6.67 (bd, 2H), 6.54 (dd, 1H, J=8.5 and 2.0 Hz), 6.37 (d, 1H, J=1.5 Hz), 5.26 (s, 2H), 2.84 (s, 3H), 2.69 (s, 3H).

Example 9

2-[1-(3,5-Difluoro-benzyl-6-methylamino-1H-indol-3-ylsulfanyl]-benzoic acid methyl ester Following a procedure analogous to that described under step vi of Example 1, 2-[6-(tert-butoxycarbonyl-methyl-amino)-1-(3,5-difluoro-benzyl)-1H-indol-3-ylsulfanyl]-benzoic acid methyl ester (Example 6, method 1, step ii; 0.100 g, 0.186 mmol) was deprotected to give, after column chromatography (dichloromethane/methanol 99:1→96:4), the title compound (0.069 g). $^1$H-NMR (DMSO-D$_6$) δ 7.93 (dd, 1H, J=7.8 and 1.6 Hz), 7.80 (m, 1H), 7.28 (ddd, 1H, =8.2, 7.4 and 1.6 Hz), 7.17 (m, 3H), 6.97 (m, 2H), 6.74 (dd, 1H, J=8.2 and 0.8 Hz), 6.71 (m, 1H), 5.48 (s, 2H), 3.90 (s, 3H), 2.87 (s, 3H).

Example 10

{2-[1-(3,5-Difluoro-benzyl-6-methylamino-1H-indol-3-ylsulfanyl]-phenyl}-methanol i)—A solution of 2-[6-(tert-butoxycarbonyl-methyl-amino)-1-(3,5-difluoro-benzyl)-1H-indol-3-ylsulfanyl]-benzoic acid methyl ester (Example 6, method 1, step ii; 0.163 g, 0.30 mmol) in a mixture of diethyl ether and tetrahydrofuran was treated with lithium aluminium hydride (1 M solution in tetrahydrofuran; 0.3 ml, 0.3 mmol). After 1 h stirring, the reaction mixture was quenched with a saturated aqueous solution of sodium sulfate. The mixture was filtered and the filtrate was concentrated under reduced pressure. Column chromatography (heptane/ethyl acetate 9:1→2:8) afforded [1-(3,5-difluoro-benzyl)-3-(2-hydroxymethyl-phenylsulfanyl)-1H-indol-6-yl]-methyl-carbamic acid tert-butyl ester (0.146 g).

ii)—Following a procedure analogous to that described under step vi of Example 1, the product obtained in the previous step (0.146 g, 0.29 mmol) was deprotected to give, after column chromatography (heptane→heptane/ethyl acetate 1:1), the title compound (0.044 g). $^1$H-NMR (CDCl$_3$) δ 7.36 (dd, 1H, J=7.4 and 1.6 Hz), 7.32 (d, 1H, J=8.8 Hz), 7.17 (s, 1H), 7.09 (td, 1H, J=7.2 and 1.6 Hz), 7.04 (td, 1H, J=7.2 and 1.6 Hz), 6.92 (dd, 1H, J=7.8 and 1.4 Hz), 6.73 (tt, 1H, = 9.0 and 2.0 Hz), 6.65 (m, 2H), 6.55 (dd, 1H, J=8.4 and 2.0 Hz), 6.34 (d, 1H, J=2.0 Hz), 5.25 (s, 2H), 4.91 (d, 2H, J=6.6 Hz), 3.78 (bs, 1H), 2.83 (s, 3H), 2.12 (t, 1H, J=6.6 Hz).

Example 11

[1-(3,5-Difluoro-benzyl)-3-(pyridin-2-ylsulfanyl)-1H-indol-6-yl]-methyl-amine i)—A solution of pyridine-2-thiol (0.072 mg, 0.65 mmol) in dichloromethane (10 ml) was cooled to 0° C. and chlorine gas was passed through the solution for 2 min. The mixture was stirred at room temperature for 15 min.; nitrogen was passed through and the mixture was concentrated under reduced pressure. A solution of [1-(3,5-difluoro-benzyl)-1H-indol-6-yl]-methyl-carbamic acid tert-butyl ester (Example 6, method 1, step i; 0.20 g, 0.54 mmol) in dichloromethane (10 ml) was added to the freshly prepared sulfenyl chloride and the reaction mixture was stirred at room temperature overnight. The mixture was poured into a saturated aqueous solution of sodium hydrogencarbonate and the product was extracted into ethyl acetate. The combined organic phases were washed with brine, dried over sodium sulfate and concentrated under reduced pressure. Column chromatography (heptane→heptane/ethyl acetate 1:1) afforded a mixture of [1-(3,5-difluoro-benzyl)-3-(pyridin-2-ylsulfanyl)-1H-indol-6-yl]-methyl-carbamic acid tert-butyl ester and [1-(3,5-difluoro-benzyl)-3-(pyridin-2-ylsulfanyl)-1H-indol-6-yl]-methyl-amine (0.279 g).

ii)—Following a procedure analogous to that described under step vi of Example 1, the mixture obtained in the previous step (0.234 g) was treated with trifluoroacetic acid to give, after column chromatography (heptane→heptane/ethyl acetate 9:1→6:4) and freeze-drying, the title compound (0.120 g). $^1$H-NMR (CDCl$_3$) δ 8.41 (bd, 1H, J=5.5 Hz), 7.39 (d, 1H, J=8.5 Hz), 7.35 (dt, 1H, J=7.5 and 2.0 Hz), 7.23 (s, 1H), 6.93 (ddd, 1H, J=7.5, 5.0 and 1.0 Hz), 6.78 (d, 1H, J=8.5 Hz), 6.73 (tt, 1H, J=8.5 and 2.5 Hz), 6.66 (bd, 2H, J=6.0 Hz), 6.58 (dd, 1H, J=8.5 and 2.0 Hz), 6.36 (d, 1H, J=1.5 Hz), 5.27 (s, 2H), 3.80 (bs, 1H), 2.84 (s, 3H).

Example 12

[1-(3,5-Difluoro-benzyl)-3-(3-nitro-pyridin-2-ylsulfanyl)-1H-indol-6-yl]-methyl-amine i)—A solution of [1-(3,5-difluoro-benzyl)-1H-indol-6-yl]-methyl-carbamic acid tert-butyl ester (Example 6, method 1, step i; 0.50 g, 0.134 mmol) in dry tetrahydrofuran (1 ml) was added to a suspension of 3-nitro-2-pyridin-2-ylsulfanyl chloride (0.031 g, 0.162 mmol) in the same solvent (1 ml). The reaction mixture was heated in a microwave apparatus at 70° C. for 10 min. and then poured into a saturated aqueous solution of sodium hydrogencarbonate. The product was extracted into ethyl acetate; the combined organic phases were washed with brine, dried over sodium sulfate and concentrated under reduced pressure. Column chromatography (heptane/ethyl acetate 9/1→6/4) afforded [1-(3,5-difluoro-benzyl)-3-(3-nitro-pyridin-2-ylsulfanyl)-1H-indol-6-yl]-methyl-carbamic acid tert-butyl ester (0.051 g).

ii)—Following a procedure analogous to that described under step vi of Example 1, the product obtained in the previous step (0.051 g, 0.097 mmol) was deprotected to give, after reversed phase HPLC (acetonitrile/water 4:6→8:2), the title compound (0.011 g). $^1$H-NMR (CDCl$_3$) δ 8.48 (dd, 1H, J=8.0 and 1.5 Hz), 8.46 (dd, 1H, J=4.5 and 1.5 Hz), 7.24 (d, 1H, J=8.5 Hz), 7.20 (s, 1H), 7.13 (dd, 1H, J=8.0 and 4.5 Hz), 6.71 (tt, 1H, J=8.5 and 2.0 Hz), 6.64-6.68 (m, 2H), 6.54 (dd, 1H, J=8.5 and 2.0 Hz), 6.35 (d, 1H, J=1.5 Hz), 5.29 (s, 2H), 2.84 (s, 3H).

Example 13

[1-(3,5-Difluoro-benzyl)-3-(2-nitro-benzenesulfonyl)-1H-indol-6-yl]-methyl-amine i)—m-Chloroperbenzoic acid (~75%, 2.03 g, ~8.8 mmol) was added to a solution of [1-(3,5-difluoro-benzyl)-3-(2-nitro-phenylsulfanyl)-1H-indol-6-yl]-methyl-carbamic acid tert-butyl ester (Example 1, step v; 2.06 g; 3.91 mmol) in dry dichloromethane (82 ml). After 10 min. stirring at room temperature, the reaction mixture was poured into a saturated aqueous solution of sodium hydrogensulfate. The product was extracted into dichloromethane; the combined organic phases were washed with a saturated aqueous solution of sodium hydrogencarbonate, water and brine, dried over magnesium sulfate and concentrated under reduced pressure. Column chromatography (heptane/ethyl acetate 3:1→6:4) afforded [1-(3,5-difluoro-benzyl)-3-(2-nitro-benzenesulfonyl)-1H-indol-6-yl]-methyl-carbamic acid tert-butyl ester (0.896 g).

ii)—Following a procedure analogous to that described under step vi of Example 1, the product obtained in the previous step (1.86 g, 3.34 mmol) was deprotected to give, after column chromatography (heptane/ethyl acetate 1:1), the title compound (1.03 g). $^1$H-NMR (DMSO-D$_6$) δ 8.27-8.30 (m, 1H), 8.14 (s, 1H), 7.91-7.98 (m, 1H), 7.82-7.89 (m, 2H), 7.44 (d, 1H, J=8.5 Hz), 7.17 (tt, 1H, J=9.2 and 2.2 Hz), 7.04 (bd, 2H, J=8.5 Hz), 6.62 (dd, 1H, J=8.7 and 2.0 Hz), 6.49 (d, 1H, J=2.0 Hz), 5.80 (q, 1H, J=5.0 Hz), 5.49 (s, 2H), 2.64 (d, 3H, J=5.0 Hz).

Example 14

Methyl-[3-(2-nitro-phenylsulfonyl)-1-pyridin-2-ylmethyl-1H-indol-6-yl]-amine

Prepared from methyl-[3-(2-nitro-phenylsulfanyl)-1-pyridin-2-ylmethyl-1H-indol-6-yl]-carbamic acid tert-butyl ester (Example 2, step v) following procedures analogous to those described under i of Example 13, and vi of Example 1, respectively. $^1$H-NMR (CDCl$_3$) δ 8.61 (dm, 1H, J=4.7 Hz), 8.39 (dd, 1H, J=7.8 and 1.4 Hz), 7.86 (s, 1H), 7.70 (m, 1H), 7.66 (d, 1H, J=8.6 Hz), 7.65 (m, 2H), 7.60 (m, 1H), 7.22 (ddd, 1H, J=7.8, 5.1 and 0.8 Hz), 6.92 (d, 1H, J=7.8 Hz), 6.63 (dd, 1H, J=8.8 and 2.0 Hz), 6.38 (d, 1H, J=2.0 Hz), 5.42 (s, 2H), 3.81 (bs, 1H), 2.77 (s, 3H).

Example 15

Following a procedure analogous to that described under vi of Example 1, the following synthetic intermediates were produced:

Example 15a 1-(3,5-Difluoro-benzyl)-3-(2-nitro-phenylsulfanyl-1H-indol-6-ylamine

[1-(3,5-Difluoro-benzyl)-3-(2-nitro-phenylsulfanyl)-1H-indol-6-yl]-carbamic acid tert-butyl ester (Example 1, step iv; 23.5 g, 46 mmol) was deprotected to give, after column chromatography (heptane/ethyl acetate 1:1), the title compound (15.2 g). $^1$H-NMR (CDCl$_3$) δ 8.26 (dd, 1H, J=8.0 and 1.5 Hz), 7.24-7.32 (m, 3H), 7.17 (dt, 1H, J=8.5 and 1.5 Hz), 7.01 (dd, 1H, J=8.0 and 1.5 Hz), 6.75 (tt, 1H, J=8.0 and 2.5 Hz), 6.65 (dd, 1H, J=7.5 and 2.0 Hz), 6.61 (dd, 1H, J=8.5 and 2.0 Hz), 6.54 (d, 1H, J=2.0 Hz), 5.26 (s, 2H), 3.73 (bs, 2H).

Example 15b 3-(2-Nitro-phenylsulfanyl)-1-pyridin-2-ylmethyl-1H-indol-6-ylamine

[3-(2-Nitro-phenylsulfanyl)-1-pyridin-2-ylmethyl-1H-indol-6-yl]-carbamic acid tert-butyl ester (Example 2, step iv; 3.4 g, 6.3 mmol) was deprotected to give, after column chromatography (heptane/ethyl acetate 2:8→ethyl acetate, containing some triethylamine), the title compound (1.54 g). $^1$H-NMR (CDCl$_3$) δ 8.62 (bd, 1H, J=5.0 Hz), 8.26 (dd, 1, J=8.0 and 1.5 Hz), 7.61 (dt, H, J=7.5 and 2.0 Hz), 7.34 (s, 1H), 7.25-7.30 (m, 2H), 7.22 (ddd, 1H, J=7.5, 5.0 and 1.0 Hz), 7.16 (ddd, 1H J=8.0, 7.0 and 1.0 Hz), 7.05 (dd, 1H, J=8.0 and 1.0 Hz), 6.86 (d, 1H, J=8.0 Hz), 6.63 (d, 1H, J=1.5 Hz), 6.60 (dd, 1H, J=8.0 and 1.5 Hz), 5.41 (s, 2H), 3.70 (bs, 2H).

Example 15c 3-(2-Nitro-phenylsulfanyl)-1-pyridin-3-ylmethyl-1H-indol-6-ylamine

[3-(2-Nitro-phenylsulfanyl)-1-pyridin-3-ylmethyl-1H-indol-6-yl]-carbamic acid tert-butyl ester (Example 3, step iv; 5.96 g, 12.5 mmol) was deprotected to give, after column chromatography (heptane/ethyl acetate/ethanol 4:4:1), the title compound (1.50 g). $^1$H-NMR (CDCl$_3$) δ 8.55-8.60 (m, 2H), 8.26 (dd, 1H, J=8.5 and 1.5 Hz), 7.42 (dt, 1H, J=8.0 and 1.5 Hz), 7.24-7.33 (m, 3H), 7.17 (ddd, 1H, J=8.0, 7.0 and 1.0 Hz), 7.01 (dd, 1H, J=8.0 and 1.5 Hz), 6.60 (m, 2H), 6.59 (s, 1H), 5.30 (s, 2H).

Example 16

Preparation of Synthetic Intermediate 2-[6-amino-1-(3,5-difluoro-benzyl-1H-indol-3-ylsulfanyl]-benzonitrile.

i)—Following a procedure analogous to that described under i of Example 6, method 2, [1-(3,5-difluoro-benzyl)-1H-indol-6-yl]-carbamic acid tert-butyl ester (Example 1, step iii; 4.00 g, 11.2 mmol) was reacted with 2-bromobenzenesulfonyl chloride to give, after column chromatography (heptane/ethyl acetate 95:5→9:1), [3-(2-bromo-phenylsulfanyl)-1-(3,5-difluoro-benzyl)-1H-indol-6-yl]-carbamic acid tert-butyl ester (5.55 g).

ii)—Following a procedure analogous to that described under ii of Example 6, method 2, the product obtained in the previous step (2.00 g, 3.67 mmol) was reacted with zinc(II) cyanide/tetrakis(triphenylphosphine)palladium(0) to give, after column chromatography (heptane/ethyl acetate 95:5→7:3), [3-(2-cyano-phenylsulfanyl)-1-(3,5-difluoro-benzyl)-1H-indol-6-yl]-carbamic acid tert-butyl ester (1.19 g).

iii)—Following a procedure analogous to that described under vi of Example 1, the product obtained in the previous step (1.19 g, 2.42 mmol) was deprotected to give, after column chromatography (heptane/ethyl acetate 3:1→65:35), the title compound (0.426 g). $^1$H-NMR (CDCl$_3$) δ 7.58 (dd, 1H, J=7.7 and 0.5 Hz), 7.34 (dd, 1H, J=8.5 and 0.5 Hz), 7.12 (dt, 1H, J=7.5 and 1.2 Hz), 6.93 (ddd, 1H, J=8.2, 1.0 and 0.5 Hz), 6.74 (tt, 1H, J=8.7 and 2.2 Hz), 6.62-6.66 (m, 2H), 6.62 (dd, 1H, J=8.5 and 2.0 Hz), 6.52 (d, 1H, J=1.7 Hz), 5.23 (s, 2H), 3.71 (bs, 2H).

Example 17

Preparation of Synthetic Intermediate 2-(6-amino-1-pyridin-2-ylmethyl-1H-indol-3-ylsulfanyl)-benzonitrile i)—Following a procedure analogous to that described under i of Example 6, method 2, (1-pyridin-2-ylmethyl-1H-indol-6-yl)-carbamic acid tert-butyl ester (Example 2, step iii; 1.44 g, 3.10 mmol) was reacted with 2-bromobenzenesulfonyl chloride to give, after column chromatography (heptane/ethyl acetate 6:4), [3-(2-bromo-phenylsulfanyl)-1-pyridin-2-ylmethyl-1H-indol-6-yl]-carbamic acid tert-butyl ester (0.715 g).

ii)—Following a procedure analogous to that described under ii of Example 6, method 2, the product obtained in the previous step (0.715 g, 1.40 mmol) was reacted with zinc(II) cyanide/tetrakis(triphenylphosphine)palladium(0) in a microwave apparatus (225 W, 200° C.) for 20 min. to give, after column chromatography (toluene/acetone 8:2), the title compound (0.217 g). $^1$H-NMR (CDCl$_3$) δ 8.63 (m, 1H), 7.72-6.50 (m, 1H), 5.39 (s, 2H), 3.69 (bs, 2H).

Example 18

[1-(3,5-Difluoro-benzyl-3-(2-nitro-phenylsulfanyl)-1H-indol-6-yl]-dimethyl-amine Iodomethane (0.568 ml, 9.12 mmol) was added to a solution of 1-(3,5-difluoro-benzyl)-3-(2-nitro-phenylsulfanyl)-1H-indol-6-ylamine (Example 15a; 2.5 g, 6.1 mmol) in a mixture of ethanol and tetrahydrofuran containing sodium carbonate (0.657 g, 6.08 mmol). The reaction mixture was heated under reflux overnight and concentrated. Water was added and the product was extracted into ethyl acetate. The combined organic phases were washed with water and brine, dried over sodium sulfate and concentrated under reduced pressure. Column chromatography (heptane/ethyl acetate 8:2) afforded [1-(3,5-difluoro-benzyl)-3-(2-nitro-phenylsulfanyl)-1H-indol-6-yl]-methyl-amine (0.647 g) and [1-(3,5-difluoro-benzyl-3-(2-nitro-phenylsulfanyl)-1H-indol-6-yl]-dimethyl-amine (0.815 g). $^1$H-NMR (CDCl$_3$) δ 8.26 (dd, 1H, J=8.2 and 1.2 Hz), 7.35 (d, 1H, J=8.6 Hz), 7.27 (ddd, 1H, J=8.2, 7.4 and 1.2 Hz), 7.25 (s, 1H), 7.17 (ddd, 1H, J=8.2, 7.4 and 1.2 Hz), 7.03 (dd, 1H, J=8.2 and 1.2 Hz), 6.78 (dd, 1H, J=8.6 and 2.3 Hz), 6.74 (tt, 1H, J=8.6 and 2.3 Hz), 6.68 (m, 2H), 6.48 (d, 1H, J=2.3 Hz), 5.29 (s, 2H), 2.95 (s, 6H).

Example 19

Following a procedure analogous to that described in Example 18 and using 1-(3,5-difluoro-benzyl)-3-(2-nitro-phenylsulfanyl)-1H-indol-6-ylamine (Example 15a), or 3-(2-nitro-phenylsulfanyl)-1-pyridin-2-ylmethyl-1H-indol-6-ylamine (Example 15b), or 3-(2-nitro-phenylsulfanyl)-1-pyridin-3-ylmethyl-1H-indol-6-ylamine (Example 15c) as starting material, the following products were prepared:

Example 19a

[1-(3,5-Difluoro-benzyl)-3-(2-nitro-phenylsulfanyl)-1H-indol-6-yl]-ethyl-amine $^1$H-NMR (CDCl$_3$) δ 8.25 (dd, 1H, J=8.2 and 1.2 Hz), 7.73 (s, 1H), 7.48 (ddd, 1H, J=8.2, 7.4 and 1.2 Hz), 7.33 (ddd, 1H, J=8.2, 7.4 and 1.2 Hz), 7.18 (tt, 1H, J=9.4 and 2.7 Hz), 7.01 (d, 1H, J=8.6 Hz), 6.99 (m, 2H), 6.92 (dd, 1H, J=8.2 and 1.2 Hz), 6.55 (d, 1H, J=1.9 Hz), 6.50 (dd, 1H, J=8.6 and 1.9 Hz), 5.55 (t, 1H, J=5.1 Hz), 5.43 (bs, 2H), 3.02 (m, 2H), 1.15 (t, 3H, J=7.4 Hz).

Example 19b

Allyl-[1-(3,5-difluoro-benzyl-3-(2-nitro-phenylsulfanyl)-1H-indol-6-yl]-amine $^1$H-NMR (CDCl$_3$) δ 8.26 (dd, 1H, J=8.2 and 1.4 Hz), 7.28 (m, 1H), 7.23 (s, 1H), 7.27 (d, 1H, J=7.8 Hz), 7.17 (ddd, 1H, J=8.6, 7.4 and 1.4 Hz), 7.03 (dd, 1H, J=8.2 and 1.2 Hz), 6.75 (tt, 1H, J=9.0 and 2.4 Hz), 6.67 (m, 2H), 6.57 (dd, 1H, J=8.6 and 2.0 Hz), 6.40 (d, 1H, J=2.0 Hz), 5.94 (ddt, J=17.2, 10.6 and 5.5 Hz), 5.27 (dq, 1H, J=16.4 and 1.6 Hz), 5.26 (s, 2H), 5.15 (dq, 1H, J=10.6 and 1.6 Hz), 3.90 (bs, 1H), 3.77 (d, 2H, J=5.1 Hz).

Example 19c

Dimethyl-[3-(2-nitro-phenylsulfanyl)-1-pyridin-2-ylmethyl-1H-indol-6-yl]-amine $^1$H-NMR (CDCl$_3$) δ 8.63 (dm, 1H, J=5.1 Hz), 8.26 (dd, 1H, J=8.2 and 1.2 Hz), 7.61 (td, 1H, J=7.8 and 2.0 Hz), 7.345 (s, 1H), 7.34 (d, 1H, J=8.6 Hz), 7.26 (m, 1H), 7.22 (dd, 1H, J=7.8 and 4.7 Hz), 7.16 (ddd, 1H, J=8.2, 7.4 and 1.2 Hz), 7.07 (dd, 1H, J=8.2 and 1.2 Hz), 6.87 (d, 1H, J=8.2 Hz), 6.77 (dd, 1H, J=8.6 and 2.3 Hz), 6.56 (d, 1H, J=2.3 Hz), 5.45 (s, 2H), 2.94 (s, 6H).

Example 19d

Ethyl-[3-(2-nitro-phenylsulfanyl)-1-pyridin-2-ylmethyl-1H-indol-6-yl]-amine $^1$H-NMR (CDCl$_3$) δ 8.62 (dm, 1H, J=5.1 Hz), 8.26 (dd, 1H, J=7.8 and 1.2 Hz), 7.61 (td, H, J=7.8 and 2.0 Hz), 7.31 (s, 1H), 7.27 (m, 1H), 7.26 (d, 1H, J=8.2 Hz), 7.22 (dd, 1H, J=7.8 and 5.1 Hz), 7.16 (ddd, 1H, J=8.2, 7.8 and 1.2 Hz), 7.07 (dd, 1H, J=8.2 and 1.2 Hz), 6.86 (d, 1H, J=8.6 Hz), 6.54 (dd, 1H, J=8.6 and 2.0 Hz), 6.46 (d, 1, J=2.0 Hz), 5.43 (s, 2H), 3.63 (bs, 1H), 3.12 (q, 2, J=7.4 Hz), 1.24 (, 31, J=7.4 Hz).

Example 19e

Dimethyl-[3-(2-nitro-phenylsulfanyl)-1-pyridin-3-ylmethyl-1H-indol-6-yl]-amine $^1$H-NMR (CDCl$_3$) δ 8.60 (d, 1H, J=2.0 Hz), 8.57 (dd, 1H, J=5.1 and 1.2 Hz), 8.26 (dd, 1H, J=8.2 and 1.6 Hz), 7.44 (dt, 1H, J=8.2 and 2.0 Hz), 7.33 (d, 1H, J=8.6 Hz), 7.28 (m, 1H), 7.26 (m, 1H), 7.26 (s, 1H), 7.16 (ddd, 1H, J=8.6, 7.4 and 1.6

Hz), 7.03 (dd, 1H, J=8.2 and 1.6 Hz), 6.77 (dd, 1H, J=8.6 and 2.0 Hz), 6.53 (d, 1H, J=2.0 Hz), 5.54 (s, 2H), 2.95 (s, 6H).

Example 20

[1-(3,5-Difluoro-benzyl)-3-(2-nitro-phenylsulfanyl)-1H-indol-6-ylamino]-acetonitrile Cesium carbonate (3.8 g, 11.7 mmol) was added to an ice-cooled solution of 1-(3,5-difluoro-benzyl)-3-(2-nitrophenylsulfanyl)-1H-indol-6-ylamine (Example 15a; 3.2 g, 7.79 mmol) in dry dimethyl formamide (15 ml). After 15 min. stirring, bromoacetonitrile (7.4 g, 62.3 mmol) was added and the reaction mixture was heated at 80° C. for 2 h. The mixture was quenched with water and the product was extracted into ethyl acetate. The combined organic phases were washed with water and brine, dried over sodium sulfate and concentrated under reduced pressure. Column chromatography (toluene/acetone 95:5) and crystallization from acetonitrile afforded the title compound (0.42 g). $^1$H-NMR (CDCl$_3$) δ 8.27 (dd, 1H, J=8.4 and 1.6 Hz), 7.37 (d, 1H, J=8.6 Hz), 7.32 (s, 1H), 7.31 (ddd, 1H, J=8.4, 7.4 and 1.6 Hz), 7.19 (ddd, 1H, J=8.4, 7.4 and 1.6 Hz), 6.99 (dd, 1H, J=8.4 and 1.6 Hz), 6.76 (tt, 1H, J=8.6 and 2.0 Hz), 6.67 (m, 2H), 6.64 (dd, 1H, J=8.6 and 2.0 Hz), 6.54 (d, 1H, J=2.0 Hz), 5.32 (s, 2H), 4.13 (d, 2H, J=6.6 Hz), 4.04 (t, 1H, J=6.6 Hz).

Example 21

Following a procedure analogous to that described in Example 20 and using 1-(3,5-difluoro-benzyl)-3-(2-nitrophenylsulfanyl)-1H-indol-6-ylamine (Example 15a), or 3-(2-nitro-phenylsulfanyl)-1-pyridin-2-ylmethyl-1H-indol-6-ylamine (Example 15b), or 3-(2-nitro-phenylsulfanyl)-1-pyridin-3-ylmethyl-1H-indol-6-ylamine (Example 15c), or 2-[6-amino-1-(3,5-difluoro-benzyl)-1H-indol-3-ylsulfanyl]-benzonitrile (Example 16), or 2-(6-amino-1-pyridin-2-ylmethyl-1H-indol-3-ylsulfanyl)-benzonitrile (Example 17), as staring material, the following products were prepared:

Example 21a

1-[1-(3,5-Difluoro-benzyl)-3-(2-nitro-phenylsulfanyl)-1H-indol-6-ylamino]-propan-2-one Alkylation was carried out with chloroacetone (2.5 equivalents), using 1.1 equivalent base. $^1$H-NMR (CDCl$_3$) δ 8.26 (dd, 1H, J=8.6 and 1.6 Hz), 7.30 (d, 1, J=8.8), 7.26 (m, 1H), 7.24 (s, 1H), 7.17 (ddd, 1H, J=8.2, 7.4 and 1.6 Hz), 7.01 (dd, 1, J=8.2 and 1.2 Hz), 6.75 (tt, 1H, J=8.8 and 2.0 Hz), 6.66 (m, 2H), 6.59 (dd, 1H, J=8.6 and 2.0 Hz), 6.33 (d, 1H, J=2.0 Hz), 5.28 (s, 2H), 4.68 (t, 1H, J=4.7 Hz), 4.00 (d, 2H, J=4.7 Hz), 2.26 (s, 3H).

Example 21b

2-[1-(3,5-Difluoro-benzyl)-3-(2-nitro-phenylsulfanyl)-1H-indol-6-ylamino]-ethanol Alkylation was carried out with 2-bromoethanol (2.2 equivalents), using 1.1 equivalent base, at 80-100° C. $^1$H-NMR (CDCl$_3$) δ 8.26 (dd, 1H, J=8.2 and 1.6 Hz), 7.29 (d, 1H, J=8.6 Hz), 7.28 (m, 1H), 7.24 (s, 1H), 7.17 (ddd, 1H, J=8.2, 7.4 and 1.6 Hz), 7.02 (dd, 1H, J=8.2 and 1.6 Hz), 6.75 (tt, 1H, J=8.8 and 2.3 Hz), 6.66 (m, 2H), 6.61 (dd, 1H, J=8.6 and 2.0 Hz), 6.45 (d, 1H, J=2.0 Hz), 5.27 (s, 2H), 4.08 (bs, 1H), 3.85 (q, 2H, J=5.1 Hz), 3.30 (t, 2H, J=5.5 Hz), 1.66 (t, 1H, J=5.5 Hz).

Example 21c

[1-(3,5-Difluoro-benzyl-3-(2-nitro-phenylsulfanyl)-1H-indol-6-yl]-(2-methoxy-ethyl)-amine Alkylation was carried out with 1-bromo-2-methoxy-ethane (1.1 equivalents), using 1.1 equivalent base, at 100° C. $^1$H-NMR (CDCl$_3$) δ 8.25 (dd, 1H, J=8.4 and 1.6 Hz), 7.28 (d, 1H, J=9.0 Hz), 7.28 (m, 1H), 7.23 (s, 1H), 7.17 (ddd, 1H, J=8.2, 7.4 and 1.6 Hz), 7.02 (dd, 1H, J=8.2 and 1.6 Hz), 6.74 (tt, 1H, J=8.8 and 2.3 Hz), 6.66 (m, 2H), 6.59 (dd, 1H, J=8.6 and 2.0 Hz), 6.42 (d, 1H, J=2.0 Hz), 5.27 (s, 2H), 4.16 (bs, 1H), 3.61 (t, 2H, J=5.5 Hz), 3.38 (s, 3H), 3.27 (t, 211, =5.5 Hz).

Example 21d

[3-(2-Nitro-phenylsulfanyl)-1-pyridin-2-ylmethyl-1H-indol-6-ylamino]-acetonitrile Alkylation was carried out with bromoacetonitrile (1.5 equivalents), using 1.1 equivalent base. $^1$H-NMR (CDCl$_3$) δ 8.63 (ddd, 1H, J=5.1, 1.8 and 1.0 Hz), 8.26 (dd, 1H, J=8.5 and 1.5 Hz), 7.63 (td, 1H, J=7.9 and 1.8 Hz), 7.41 (s, 1H), 7.35 (d, 1H, J=8.9 Hz), 7.29 (ddd, 1H, J=8.5, 7.1 and 1.5 Hz), 7.24 (ddd, 1H, J=7.7, 4.8 and 1.0 Hz), 7.18 (ddd, 1H, J=8.6, 7.3 and 1.5 Hz), 7.01 (dd, 1H, J=8.3 and 1.2 Hz), 6.94 (dt, 1H, J=8.1 and 1.0 Hz), 6.66 (d, 1H, J=2.0 Hz), 6.61 (dd, 11, J=8.6 and 2.2 Hz), 5.46 (s, 2H), 4.12 (d, 2H, J=7.1 Hz), 4.01 (t, 1H, J=7.5 Hz).

Example 21e (2-Methoxy-ethyl)-[3-(2-nitro-phenylsulfanyl)-1-pyridin-2-ylmethyl-1H-indol-6-yl]-amine Alkylation was carried out with 1-bromo-2-methoxy-ethane (1.1 equivalents), using 1.0 equivalent base, in dimethyl acetamide, at 100-140° C. $^1$H-NMR (CDCl$_3$) δ 8.62 (dm, 1H, J=8.2 Hz), 8.25 (dd, 1H, J=8.2 and 1.6 Hz), 7.61 (td, 1H, J=7.8 and 2.0 Hz), 7.32 (s, 1H), 7.27 (d, 1H, J=8.6 Hz), 7.27 (m, 1H), 7.22 (ddd, 1H, J=7.8, 4.9 and 1.0 Hz), 7.17 (ddd, 1H, J=8.2, 7.4 and 1.6 Hz), 7.06 (dd, 1H, J=8.6 and 1.6 Hz), 6.85 (d, 1H, J=8.2 Hz), 6.58 (dd, 1H, J=8.6 and 2.0 Hz), 6.50 (d, H, J=2.0 Hz), 5.43 (s, 2H), 3.59 (t, 2H, J=5.1 Hz), 3.37 (s, 3H), 3.25 (t, 2H, J=5.1 Hz), 1.58 (bs, 1H).

Example 21f (2-Methoxy-ethyl)-[3-(2-nitro-phenylsulfanyl)-1-pyridin-3-ylmethyl-1H-indol-6-yl]-amine Alkylation was carried out with toluene-4-sulfonic acid 2-methoxy-ethyl ester (1.7 equivalents), using 1.2 equivalent base. $^1$H-NMR (CDCl$_3$) δ 8.59 (d, 1H, J=2.0 Hz), 8.57 (dd, 1H, J=5.0 and 2.0 Hz), 8.25 (dd, 1H, J=8.5 and 1.5 Hz), 7.43 (dt, 1H, J=8.0 and 2.0 Hz), 7.21-7.31 (m, 4H), 7.16 (ddd, 1H, J=8.0, 7.0 and 1.0 Hz), 7.02 (dd, 1H, J=8.5 and 1.5 Hz), 6.58 (dd, 1H, J=8.5 and 2.0 Hz), 6.46 (d, 1H, J=2.0 Hz), 5.32 (s, 2H), 3.61 (t, 2H, J=5.5 Hz), 3.38 (s, 3H), 3.27 (t, 2H, J=5.5 Hz).

Example 21g

2-[6-(Cyanomethyl-amino)-1-(3,5-difluoro-benzyl)-1H-indol-3-ylsulfanyl]-benzonitrile Alkylation was carried out with bromoacetonitrile (1.5 equivalents), using 1.1 equivalent base. $^1$H-NMR (CDCl$_3$) δ 7.59 (dd, 1H, J=7.3 and 1.5 Hz) 7.44 (d, 1H, J=8.7 Hz), 7.34 (s, 1H), 7.23-7.32 (m, 1H), 7.13 (dt, 1H, J=7.5 and 1.0 Hz), 6.92 (dd, 1H, J=8.2 and 1.0 Hz), 6.76 (tt, 1H, J=8.7 and 2.2 Hz), 6.68 (m, 2H), 6.64 (dd, 1H, J=8.7 and 2.0 Hz), 6.52 (d, 1H, J=2.0 Hz), 5.30 (s, 2H), 4.12 (d, 1H, J=5.0 Hz), 4.02 (t, 1H, J=5.0 Hz).

Example 21h

2-[1-(3,5-Difluoro-benzyl-6-(2-hydroxy-ethylamino)-1H-indol-3-ylsulfanyl]-benzonitrile Alkylation was carried out with 2-bromoethanol (1.5 equivalents), using 1.1 equivalent base. $^1$H-NMR (CDCl$_3$) δ 7.58 (dd, 1H, J=7.7 and 1.5 Hz), 7.36 (d, 1H, J=8.7 Hz), 7.24-7.32 (m, 2H), 7.11 (dt, 1H, J=7.5 and 1.2 Hz), 6.93 (d, 1H, J=8.0 Hz), 6.74 (tt, 1H, J=8.5 and 2.4 Hz), 6.60-6.69 (m, 3H), 6.43 (d, 1H, J=1.8 Hz), 5.25 (s, 2H), 4.08 (bs, 1H), 3.85 (bs, 2H), 3.30 (m, 2H).

Example 21i

2-[1-(3,5-Difluoro-benzyl-6-(2-methoxy-ethylamino)-1H-indol-3-ylsulfanyl]-benzonitrile Alkylation was carried out with toluene-4-sulfonic acid 2-methoxy-ethyl ester (2.2 equivalents), using 1.1 equivalent base. $^1$H-NMR (CDCl$_3$) δ 7.58 (dd, 1H, J=7.5 and 1.5 Hz), 7.38 (d, 1H, J=8.5 Hz), 7.28 (dd, 1H, J=7.5 and 1.5 Hz), 7.25 (d, 1H, J=8.5 Hz), 7.11 (dt, 1H, J=7.5 and 1.0 Hz), 6.93 (d, 1H, J=7.5 Hz), 6.75 (tt, 1H, J=8.4 and 2.5 Hz), 6.65 (bd, 2H, J=5.5 Hz), 6.60 (dd, 1H, J=8.9 and 2.0 Hz), 6.40 (d, 1H, J=2.0 Hz), 5.25 (s, 2H), 4.12 (bs, 1H), 3.61 (t, 2H, J=5.0 Hz), 3.38 (s, 3H), 3.27 (t, 2H, J=5.0 Hz).

Example 21j

[3-(2-Nitro-phenylsulfanyl)-1-pyridin-3-ylmethyl-1H-indol-6-ylamino]-acetonitrile Alkylation was carried out with bromoacetonitrile (2 equivalents), using 1.5 equivalent of base. $^1$H-NMR (CDCl$_3$) δ 8.56-8.65 (m, 2H), 8.26 (dd, 1H, J=8.2 and 1.2 Hz), 7.50 (bd, 1H, J=7.7 Hz), 7.35 (d, 1H, J=8.5 Hz), 7.32 (s, 1H), 7.27-7.32 (m, 2H), 7.18 (ddd, 1H, J=8.2, 7.2 and 1.0 Hz), 6.98 (dd, 1H, J=8.3 and 1.0 Hz), 6.59-6.65 (m, 2H), 5.37 (s, 2H), 4.13 (s, 2H).

Example 21k

[1 (3,5-Difluoro-benzyl)-3-(2-nitro-phenylsulfanyl)-1H-indol-6-yl]-(2,2,2-trifluoroethyl)-amine A mixture of 1-(3,5-difluoro-benzyl)-3-(2-nitro-phenylsulfanyl)-1H-indol-6-ylamine (Example 15a; 0.103 g, 0.25 mmol) and trifluoroacetaldehyde ethyl hemiacetal (0.023 ml, 0.25 mmol) in dimethylformamide (1 ml) was heated in a microwave apparatus (200 W, 100° C.) for 1 hour. After addition of another equivalent of trifluoroacetaldehyde ethyl hemiacetal the reaction mixture was heated in a microwave apparatus (200 W, 100° C.) for 1 hour more. Sodium cyanoborohydride (0.016 g, 0.25 mmol) was added. The reaction mixture was stirred at room temperature for 3 hours and then poured into ethyl acetate, washed with aqueous hydrochloric acid solution (0.1 M), a saturated aqueous solution of sodium hydrogen carbonate and brine. The organic phase was dried over sodium sulfate and concentrated under reduced pressure. Reversed phase HPLC (acetonitril/water/trifluoroacetic acid 47/50/3→97/0/3) afforded [1-(3,5-difluorobenzyl)-3-(2-nitro-phenylsulfanyl)-1H-indol-6-yl]-(2,2,2-trifluoro-ethyl)-amine (0.008 g). $^1$H-NMR (CDCl$_3$) δ 8.26 (dd, 1H, J=8.2 and 1.2 Hz), 7.33 (d, 1H, J=8.5 Hz), 7.26-7.31 (m, 2H), 7.18 (ddd, 1H, J=8.2, 7.2 and 1.1 Hz), 7.00 (dd, 1H, J=8.2 and 1.1 Hz), 6.76 (tt, 1H, J=8.7 and 2.2 Hz), 6.64-6.68 (m, 2H), 6.62 (dd, 1H, J=8.5 and 2.0 Hz), 6.50 (d, 1H, J=2.0 Hz), 5.29 (s, 2H), 3.77 (q, 2H, J=8.9 Hz).

Example 22

Using [1-(3,5-difluoro-benzyl)-3-(2-nitro-phenylsulfanyl)-1H-indol-6-yl]-carbamic acid tert-butyl ester (Example 1, step iv), [3-(2-nitro-phenylsulfanyl)-1-pyridin-2-ylmethyl-1H-indol-6-yl]-carbamic acid tert-butyl ester (Example 2, step iv), or [3-(2-nitro-phenylsulfanyl)-1-pyridin-3-ylmethyl-1H-indol-6-yl]-carbamic acid tert-butyl ester (Example 3, step iv) as staring material, and following procedures analogous to those described under steps v and vi, under Example 1, the following products were prepared:

Example 22a

[1-(3,5-Difluoro-benzyl)-3-(2-nitro-phenylsulfanyl)-1H-indol-6-yl]-propyl-amine $^1$H-NMR (CDCl$_3$) δ 8.26 (dd, 1H, J=8.4 and 1.6 Hz), 7.27 (m, 1H), 7.26 (d, 1H, J=8.6 Hz), 7.22 (s, 1H), 7.17 (ddd, 1H, J=8.2, 7.4 and 1.6 Hz), 7.03 (dd, 1H, J=8.2 and 1.4 Hz), 6.74 (tt, 1H, J=8.8 and 2.3 Hz), 6.67 (m, 2H), 6.55 (dd, 1H, J=8.6 and 2.0 Hz), 6.37 (d, 1H, J=2.0 Hz), 5.27 (s, 2H), 3.73 (bs, 1H), 3.06 (t, 2H, J=7.2 Hz), 1.65 (hextet, 2H, J=7.2 Hz), 1.00 (t, 3H, J=7.2 Hz).

Example 22b

[1-(3,5-Difluoro-benzyl)-3-(2-nitro-phenylsulfanyl)-1H-indol-6-yl]-prop-2-ynyl-amine $^1$H-NMR (CDCl$_3$) δ 8.26 (dd, 1H, J=8.2 and 1.6 Hz), 7.31 (d, 1H, J=8.6 Hz), 7.28 (m, 1H), 7.26 (s, 1H), 7.17 (ddd, 1H, J=8.2, 7.4 and 1.6 Hz), 7.01 (dd, 1H, J=8.2 and 1.6 Hz), 6.74 (tt, 1H, J=8.8 and 2.3 Hz), 6.70 (m, 2H), 6.61 (dd, 1H, J=8.6 and 2.0 Hz), 6.55 (d, 1H, J=2.0 Hz), 5.29 (s, 2H), 4.00 (m, 1H), 3.95 (m, 2H), 2.19 (t, 1H, J=2.3 Hz).

Example 22c

[1-(3,5-Difluoro-benzyl-3-(2-nitro-phenylsulfanyl)-1H-indol-6-yl]-(2-methyl-allyl)-amine.

$^1$H-NMR (CDCl$_3$) δ 8.25 (dd, 1H, J=8.2 and 1.4 Hz), 7.28 (ddd, 1H, J=8.2, 7.4 and 1.6 Hz), 7.25 (d, 1H, J=8.6 Hz), 7.23 (s, 1H), 7.16 (ddd, 1H, J=8.2, 7.4 and 1.6 Hz), 7.04 (dd, 1H, J=8.2 and 1.4 Hz), 6.75 (tt, 1H, J=8.8 and 2.3 Hz), 6.67 (m, 2H), 6.56 (dd, 1H, J=8.6 and 2.0 Hz), 6.36 (d, 1H, J=2.0 Hz), 5.24 (s, 2H), 4.94 (s, 1H), 4.86 (q, 1H, J=1.2 Hz), 4.00 (bs, 1H), 3.67 (s, 2H), 1.76 (s, 3H).

Example 22d

Cyclopropylmethyl-[1-(3,5-difluoro-benzyl-3-(2-nitro-phenylsulfanyl)-1H-indol-6-yl]-amine.

$^1$H-NMR (CDCl$_3$) δ 8.26 (dd, 1H, J=8.6 and 1.6 Hz), 7.27 (d, 1H, J=8.2 Hz), 7.27 (ddd, 1H, J=8.2, 7.4 and 1.6 Hz), 7.22 (s, 1H), 7.16 (ddd, 1H, J=8.2, 7.4 and 1.6 Hz), 7.02 (dd, 1H, J=8.2 and 1.6 Hz), 6.74 (tt, 1H, J=9.0 and 2.3 Hz), 6.66 (m, 2H), 6.57 (dd, 1H, J=8.4 and 2.0 Hz), 6.36 (d, 1H, J=2.0 Hz), 5.26 (s, 2H), 3.94 (bs, 1H), 2.94 (d, 2H, J=7.01 Hz), 1.09 (m, 1H), 0.46 (dd, 1H, J=5.9 and 4.7 Hz), 0.44 (dd, 1H, J=5.9 and 4.7 Hz), 0.24 (t, 1H, J=4.7 Hz), 0.23 (t, 1H, J=4.7 Hz).

Example 22e

[1-(3,5-Difluoro-benzyl-3-(2-nitro-phenylsulfanyl)-1H-indol-6-ylamino]-acetic acid methyl ester.

$^1$H-NMR (CDCl$_3$) δ 8.26 (dd, 1H, J=8.2 and 1.6 Hz), 7.31 (d, 1H, J=8.6 Hz), 7.28 (ddd, 1H, J=8.6, 7.4 and 1.6 Hz), 7.25 (s, 1H), 7.17 (ddd, 1H, J=8.6, 7.4 and 1.6 Hz), 7.01 (dd, 1H, J=8.2 and 1.6 Hz), 6.75 (tt, 1H, J=8.8 and 2.3 Hz), 6.66 (m, 2H), 6.60 (dd, 1H, J=8.6 and 2.0 Hz), 6.36 (d, 1H, J=2.0 Hz), 5.27 (s, 2H), 4.38 (t, 1H, J=5.9 Hz), 3.92 (d, 2H, J=5.5 Hz), 3.77 (s, 3H).

Example 23

Hydrochloride Salt of methyl-[3-(2-nitro-phenylsulfanyl)-1-pyridin-2-ylmethyl-1H-indol-6-yl]-amine A solution of methyl-[3-(2-nitro-phenylsulfanyl)-1-pyridin-2-ylmethyl-1H-indol-6-yl]-amine (Example 2, 5.14 g, 13.2 mmol) in acetone (350-400 ml) was treated with hydrochloric acid (2 M solution in methanol; 20 ml, 40 mmol). The product immediately starts to precipitate. The crystals were collected by filtration, washed with acetone and pentane and dried under reduced pressure, to afford the hydrochloride salt of methyl-[3-(2-nitro-phenylsulfanyl-1-pyridin-2-ylmethyl-1H-indol-6-yl]-amine (5.62 g). $^1$H-NMR (CD$_3$OD) δ 8.80 (dm, 1, J1=5.7 Hz), 8.32 (td, 1H, J=8.1 and 1.6 Hz), 8.26 (dd, 1H, J=8.4 and 1.6 Hz), 8.03 (s, 1H), 7.84 (m, 1H), 7.82 (m, 1H), 7.62 (d, 1H, J=8.8 Hz), 7.51 (d, 1H, J=8.2 Hz), 7.36 (ddd, 1H, J=8.4, 7.4 and 1.6 Hz), 7.30 (ddd, 1H, J=8.4, 7.4 and 1.5 Hz), 7.27 (dd, 1H, J=8.7 and 2.0 Hz), 6.98 (dd, 1H, J=8.5 and 1.5 Hz), 5.98 (bs, 2H), 3.11 (s, 3H).

Example 24

Following a procedure analogous to that described under Example 23, the following products were prepared:

Example 24a

Hydrochloride salt of [1-(3,5-difluoro-benzyl-3-(2-nitro-phenylsulfanyl)-1H-indol-6-yl]-methyl-amine.

Prepared from the free base (Example 1). $^1$H-NMR (CD$_3$OD) δ 8.26 (dd, 1H, J=8.2 and 1.6 Hz), 8.01 (s, 1H), 7.65 (d, 1H, J=2.0 Hz), 7.60 (d, 1H, J=8.6 Hz), 7.34 (m, 1H), 7.28 (m, 1H), 7.24 (dd, 1H, J=8.8 and 2.0 Hz), 6.92 (tt, 1H, J=9.4 and 2.3 Hz), 6.89 (dd, 1H, J=7.8 and 1.6 Hz), 6.86 (m, 2H), 5.62 (s, 2H), 3.10 (s, 3H).

Example 24b

Hydrochloride salt of [1-(3,5-difluoro-benzyl)-3-(2-nitro-phenylsulfanyl)-1H-indol-6-yl]-dimethyl-amine.

Prepared from the free base (Example 18). $^1$H-NMR (CD$_3$OD) δ 8.26 (dd, 1H, J=8.2 and 2.0 Hz), 7.98 (s, 1H), 7.74 (bs, 1H), 7.59 (d, 1H, J=8.8 Hz), 7.30 (m, 3H), 6.90 (m, 4H), 5.62 (s, 2H), 4.89 (s, 6H).

Example 24c

Hydrochloride salt of methyl-[3-(2-nitro-phenylsulfanyl)-1-pyridin-3-ylmethyl-1H-indol-6-yl]-amine.

Prepared from the free base (Example 3). $^1$H-NMR (CD$_3$OD) δ 8.81 (m, 1H), 8.80 (d, 1H, J=5.4 Hz), 8.34 (d, 1H, J=8.5 Hz), 8.27 (dd, 1H, J=8.1 and 1.6 Hz), 8.04 (s, 1H), 7.98 (dd, 1H, J=8.1 and 5.8 Hz), 7.80 (d, 1H, J=1.9 Hz), 7.60 (d, 1H, J=8.5 Hz), 7.36 (ddd, 1H, J=8.5, 7.8 and 1.6 Hz), 7.29 (ddd, 1H, J=8.5, 7.8 and 1.6 Hz), 7.25 (dd, 1H, J=8.1 and 1.9 Hz), 6.94 (dd, 1H, J=8.1 and 1.9 Hz), 5.86 (s, 2H), 3.12 (s, 3H), 2.77 (bs, 1H).

Example 24d

Hydrochloride salt of methyl-[3-(2-nitro-phenylsulfanyl)-1-pyridin-4-ylmethyl-1H-indol-6-yl]-amine.

Prepared from the free base (Example 5e). $^1$H-NMR (CD$_3$OD) δ 8.57 (d, 2H, J=6.0 Hz), 8.25 (dd, 1H, J=8.0 and 1.5 Hz), 7.39 (s, 1H), 7.40 (d, 1H, J=9.0 Hz), 7.38-7.31 (m, 3H), 7.28 (dt, 1H, J=8.5 and 1.5 Hz), 7.09 (bs, 1H), 6.99 (dd, 1H, J=8.5 and 1.5 Hz), 6.95 (dd, 1H, J=9.0 and 1.5 Hz), 5.69 (s, 2H), 2.92 (s, 3H).

Example 25

Androgen Activity

The androgenic activity (potency) of the compounds of the invention was determined in an in vitro bioassay of Chinese hamster ovary (CHO) cells stably transfected with the human androgen receptor expression plasmid and a reporter plasmid in which the MMTV promoter is linked to the luciferase reporter gene. The cell line CHO-AR-pMMTV-LUC 1G12-A5-CA is described in Schoonen et al. (J. Steroid Biochem. Molec. Biol. 2002; 74: 213-222). The androgen receptor activity of compounds was determined in the presence of 0.1 µmol/l onapristone. The maximal efficacy in the presence of 100 nmol/1 DHT was set as 100%. The potencies are expressed as percentage of DHT activity. Results are collected in Table 1.

TABLE 1

Androgenic activity of the compounds of the invention.

| Example | R¹ | R² | R³ | R⁴ | X | Potency (%) |
|---|---|---|---|---|---|---|
| 1 | CH₃ | H | 3,5-difluorophenyl | 2-nitro-phenyl | S | 15.0 |
| 2 | CH₃ | H | pyridin-2-yl | 2-nitro-phenyl | S | 9.9 |
| 3 | CH₃ | H | pyridin-3-yl | 2-nitro-phenyl | S | 13.4 |
| 5a | CH₃ | H | phenyl | 2-nitro-phenyl | S | 9.2 |
| 5b | CH₃ | H | 2-fluorophenyl | 2-nitro-phenyl | S | 0.4 |
| 5c | CH₃ | H | 3-fluorophenyl | 2-nitro-phenyl | S | 13.3 |
| 5d | CH₃ | H | 4-fluorophenyl | 2-nitro-phenyl | S | 4.3 |
| 5e | CH₃ | H | pyridin-4-yl | 2-nitro-phenyl | S | 35.1 |
| 5f | CH₃ | H | pyrimidin-2-yl | 2-nitro-phenyl | S | 1.8 |
| 5g | CH₃ | H | pyrimidin-5-yl | 2-nitro-phenyl | S | 21.6 |
| 5h | CH₃ | H | furan-2-yl | 2-nitro-phenyl | S | 16.5 |
| 5i | CH₃ | H | furan-3-yl | 2-nitro-phenyl | S | 17.9 |
| 5j | CH₃ | H | oxazol-4-yl | 2-nitro-phenyl | S | 14.8 |
| 5k | CH₃ | H | isoxazol-3-yl | 2-nitro-phenyl | S | 11.9 |
| 5l | CH₃ | H | thiazol-4-yl | 2-nitro-phenyl | S | 4.8 |
| 5m | CH₃ | H | oxazol-2-yl | 2-nitro-phenyl | S | 3.2 |
| 5n | CH₃ | H | isoxazol-5-yl | 2-nitro-phenyl | S | 19.4 |
| 5o | CH₃ | H | 3-methylphenyl | 2-nitro-phenyl | S | 1.6 |
| 5p | CH₃ | H | 3-chlorophenyl | 2-nitro-phenyl | S | 1.3 |
| 5q | CH₃ | H | 3-CF₃-phenyl | 2-nitro-phenyl | S | 1.0 |
| 5r | CH₃ | H | 3-cyanophenyl | 2-nitro-phenyl | S | 11.4 |
| 5s | CH₃ | H | 3,5-dicyanophenyl | 2-nitro-phenyl | S | 5.9 |
| 6 | CH₃ | H | 3,5-difluorophenyl | 2-cyano-phenyl | S | 10.5 |
| 7 | CH₃ | H | pyridin-2-yl | 2-cyano-phenyl | S | 1.1 |
| 8 | CH₃ | H | 3,5-difluorophenyl | 2-acetyl-phenyl | S | 0.2 |
| 9 | CH₃ | H | 3,5-difluorophenyl | 2-(methoxycarbonyl)-phenyl | S | 0.7 |
| 10 | CH₃ | H | 3,5-difluorophenyl | 2-(hydroxymethyl)phenyl | S | 4.3 |
| 11 | CH₃ | H | 3,5-difluorophenyl | pyridin-2-yl | S | 6.6 |
| 12 | CH₃ | H | 3,5-difluorophenyl | 3-nitro-pyridin-2-yl | S | 5.7 |
| 13 | CH₃ | H | 3,5-difluorophenyl | 2-nitro-phenyl | SO₂ | 18.9 |
| 14 | CH₃ | H | pyridin-2-yl | 2-nitro-phenyl | SO₂ | 1.9 |
| 18 | CH₃ | CH₃ | 3,5-difluorophenyl | 2-nitro-phenyl | S | 2.7 |
| 19a | CH₂CH₃ | H | 3,5-difluorophenyl | 2-nitro-phenyl | S | 2.7 |
| 19b | CH₂CH=CH₂ | H | 3,5-difluorophenyl | 2-nitro-phenyl | S | 2.4 |
| 19c | CH₃ | CH₃ | pyridin-2-yl | 2-nitro-phenyl | S | 1.2 |
| 19d | CH₂CH₃ | H | pyridin-2-yl | 2-nitro-phenyl | S | 6.7 |
| 19e | CH₃ | CH₃ | pyridin-3-yl | 2-nitro-phenyl | S | 2.6 |
| 20 | CH₂CN | H | 3,5-difluorophenyl | 2-nitro-phenyl | S | 40.2 |
| 21a | CH₂C(O)CH₃ | H | 3,5-difluorophenyl | 2-nitro-phenyl | S | 7.2 |
| 21b | CH₂CH₂OH | H | 3,5-difluorophenyl | 2-nitro-phenyl | S | 7.9 |
| 21c | CH₂CH₂OCH₃ | H | 3,5-difluorophenyl | 2-nitro-phenyl | S | 11.4 |
| 21d | CH₂CN | H | pyridin-2-yl | 2-nitro-phenyl | S | 6.7 |
| 21e | CH₂CH₂OCH₃ | H | pyridin-2-yl | 2-nitro-phenyl | S | 8.3 |
| 21f | CH₂CH₂OCH₃ | H | pyridin-3-yl | 2-nitro-phenyl | S | 20.9 |
| 21g | CH₂CN | H | 3,5-difluorophenyl | 2-cyano-phenyl | S | 9.2 |
| 21h | CH₂CH₂OH | H | 3,5-difluorophenyl | 2-cyano-phenyl | S | 2.9 |
| 21i | CH₂CH₂OCH₃ | H | 3,5-difluorophenyl | 2-cyano-phenyl | S | 6.0 |
| 21j | CH₂CN | H | pyridin-3-yl | 2-nitro-phenyl | S | 1.0 |
| 21k | CH₂CF₃ | H | 3,5-difluorophenyl | 2-nitro-phenyl | S | 0.6 |
| 22a | CH₂CH₂CH₃ | H | 3,5-difluorophenyl | 2-nitro-phenyl | S | 2.4 |
| 22b | CH₂C≡CH | H | 3,5-difluorophenyl | 2-nitro-phenyl | S | 27.1 |
| 22c | CH₂C(CH₃)=CH₂ | H | 3,5-difluorophenyl | 2-nitro-phenyl | S | 1.2 |
| 22d | cyclopropylmethyl | H | 3,5-difluorophenyl | 2-nitro-phenyl | S | 0.9 |
| 22e | CH₂C(O)OCH₃ | H | 3,5-difluorophenyl | 2-nitro-phenyl | S | 4.0 |

The invention claimed is:

1. A compound of formula I:

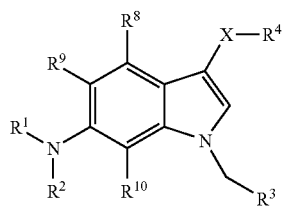

formula I wherein

X is S or SO₂;

R¹ is (1C-6C)alkyl, (3C-6C)alkenyl, or (3C-6C)alkynyl, each optionally substituted with (3C-6C)cycloalkyl, OH, OC(O)(1C-4C)alkyl, (1C-4C)alkoxy, halogen, cyano, formyl, C(O)(1C-4C)alkyl, CO₂H, CO₂(1C-4C)alkyl, C(O)NR⁵R⁶, S(O)(1C-4C)alkyl or S(O)₂(1C-4C)alkyl;

R² is hydrogen, (1C-4C)alkyl or C(O)(1C-4C)alkyl;

R³ is pyridyl optionally substituted with (1C-4C)alkyl, (1C-4C)fluoroalkyl, (1C-4C)alkoxy, halogen or cyano;

R⁴ is a phenyl group, substituted at the ortho position with 1-hydroxy(1C-4C)alkyl, (1C-4C)alkoxy, C(O)(1C-4C)alkyl, CO₂(1C-4C)alkyl, C(O)NH₂, cyano, nitro, or CH=NOR⁷, and optionally further substituted with (1C-2C)alkyl, (1C-2C)fluoroalkyl or halogen;

R⁵ and R⁶ are independently hydrogen or (1C-4C)alkyl;

$R^7$ is hydrogen or C(O)(1C-4C)alkyl;

$R^8$, $R^9$, $R^{10}$ are independently hydrogen, (1C-2C)alkyl, fluoro or chloro;

or a salt thereof.

2. A compound according to claim 1, wherein $R^8$, $R^9$, $R^{10}$ are hydrogen.

3. A compound according to claim 2, wherein $R^2$ is hydrogen, (1C-2C)alkyl or C(O)CH$_3$;

$R^3$ is pyridyl optionally substituted with (1C-2C)alkyl, (1C-2C)fluoroalkyl, (1C-2C)alkoxy, halogen or cyano;

$R^4$ is a phenyl group, substituted at the ortho position with hydroxymethyl, methoxy, C(O)CH$_3$, CO$_2$CH$_3$, C(O)NH$_2$, cyano, nitro or CH=NOR$^7$, and optionally further substituted with (1C-2C)alkyl, (1C-2C)fluoroalkyl or halogen; and $R^7$ is hydrogen or C(O)(1C-2C)alkyl.

4. A compound according to claim 3, wherein

X is S;

$R^1$ is (1C-4C)alkyl, (3C-6C)alkenyl, or (3C-6C)alkynyl, each optionally substituted with (3C-6C)cycloalkyl, OH, OC(O)(1C-2C)alkyl, (1C-2C)alkoxy, halogen, cyano, formyl, C(O)(1C-2C)alkyl, CO$_2$H or CO$_2$(1C-2C)alkyl;

$R^3$ is pyridyl optionally substituted with methyl, CF$_3$, methoxy, fluoro, chloro or cyano;

$R^4$ is a phenyl group, substituted at the ortho position with hydroxymethyl, methoxy, C(O)CH$_3$, CO$_2$CH$_3$, C(O)NH$_2$, cyano, nitro or CH=NOH.

5. A compound according to claim 4, wherein $R^2$ is hydrogen.

6. A compound according to claim 5, wherein $R^3$ is pyridyl optionally substituted with methyl, CF$_3$, methoxy, fluoro, chloro or cyano.

7. A compound according to claim 6, wherein $R^4$ is a phenyl group substituted at the ortho position with hydroxymethyl, methoxy, C(O)CH$_3$, CO$_2$CH$_3$, C(O)NH$_2$, cyano, nitro or CH=NOH.

8. A compound according to claim 7, wherein $R^1$ is (1C-4C)alkyl optionally substituted with OH, (1C-2C)alkoxy, cyano, C(O)(1C-2C)alkyl or CO$_2$(1C-2C)alkyl;

$R^3$ is pyridyl optionally substituted with methyl, fluoro, chloro or cyano; and $R^4$ is a phenyl group, substituted at the ortho position with hydroxymethyl, cyano or nitro.

9. A compound according to claim 8, wherein $R^3$ is selected from the group consisting of pyridin-2-yl, pyridin-3-yl, and pyridin-4-yl, each optionally substituted with methyl, fluoro, chloro or cyano.

10. A compound according to claim 9, wherein $R^1$ is (1C-4C)alkyl optionally substituted with methoxy, cyano, C(O)CH$_3$ or CO$_2$CH$_3$;

$R^3$ is selected from the group consisting of pyridin-2-yl, pyridin-3-yl, and pyridin-4-yl; and $R^4$ is a 2-nitrophenyl group.

11. A compound according to claim 10 which is methyl-[3-(2-nitro-phenylsulfanyl)-1-pyridin-2-ylmethyl-1H-indol-6-yl]-amine; or methyl-[3-(2-nitro-phenylsulfanyl)-1-pyridin-3-ylmethyl-1H-indol-6-yl]-amine.

12. A pharmaceutical composition comprising a compound according to claim 1 or a salt thereof and a pharmaceutically acceptable carrier.

13. A method of treating male hypogonadism comprising administering a pharmaceutically effective amount of a compound according to claim 1 or a salt thereof to a subject in need thereof.

* * * * *